United States Patent
Xu et al.

(10) Patent No.: US 12,042,554 B2
(45) Date of Patent: *Jul. 23, 2024

(54) COMPOSITIONS AND METHODS FOR BLOCKING ULTRAVIOLET RADIATION

(71) Applicant: THE REGENTS OF THE UNIVERSITY OF MICHIGAN, Ann Arbor, MI (US)

(72) Inventors: X. Z. Shawn Xu, Ann Arbor, MI (US); Jianfeng Liu, Wuhan (CN)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 18/169,971

(22) Filed: Feb. 16, 2023

(65) Prior Publication Data

US 2023/0255874 A1    Aug. 17, 2023

Related U.S. Application Data

(63) Continuation of application No. 17/122,358, filed on Dec. 15, 2020, now Pat. No. 11,744,790, which is a continuation of application No. 16/349,448, filed as application No. PCT/US2017/061305 on Nov. 13, 2017, now Pat. No. 10,864,153.

(60) Provisional application No. 62/421,672, filed on Nov. 14, 2016.

(51) Int. Cl.
| | |
|---|---|
| *A61K 8/64* | (2006.01) |
| *A61K 9/00* | (2006.01) |
| *A61K 38/17* | (2006.01) |
| *A61Q 17/04* | (2006.01) |

(52) U.S. Cl.
CPC .............. *A61K 8/64* (2013.01); *A61K 9/0014* (2013.01); *A61K 38/1767* (2013.01); *A61Q 17/04* (2013.01); *A61K 2800/10* (2013.01); *A61K 2800/86* (2013.01)

(58) Field of Classification Search
CPC ................................ A61K 8/64; A61K 9/0014
See application file for complete search history.

(56) References Cited

U.S. PATENT DOCUMENTS

| | | | |
|---|---|---|---|
| 10,864,153 B2 | 12/2020 | Xu et al. | |
| 2012/0172413 A1 | 7/2012 | Dillin et al. | |
| 2015/0093342 A1 | 4/2015 | Domloge et al. | |
| 2019/0336430 A1 | 11/2019 | Xu et al. | |

FOREIGN PATENT DOCUMENTS

WO    WO 2018/089893    5/2018

OTHER PUBLICATIONS

Goya et al., 2016, Circadian rhythms identified in Caenorhabditis elegans by in vivo long-term monitoriung of a bioluminescent reporter, PNAS, E7837-E7845.*
Bellono et al., "UV light phototransduction activates transient receptor potential A1 ion channels in human melanocytes." Proc Natl Acad Sci U S A. Feb. 5, 2013;110(6):2383-8.
Benton et al., "Atypical membrane topology and heteromeric function of *Drosophila* odorant receptors in vivo." PLoS Biol. Feb. 2006;4(2):e20.
Bhatla et al., "Light and hydrogen peroxide inhibit C. elegans Feeding through gustatory receptor orthologs and pharyngeal neurons." Neuron. Feb. 18, 2015;85(4):804-18. 43 pages.
Christensen et al., "A primary culture system for functional analysis of C. elegans neurons and muscle cells." Neuron. Feb. 14, 2002;33(4):503-14.
Debono et al., "Neuronal substrates of complex behaviors in C. elegans." Annu Rev Neurosci. 2005;28:451-501.
Dutta et al., "Characterization of membrane protein non-native states. 2. The SDS-unfolded states of rhodopsin." Biochemistry. Aug. 3, 2010;49(30):6329-40.
Edwards et al. "A novel molecular solution for ultraviolet light detection in Caenorhabditis elegans." PLoS Biol. Aug. 5, 2008;6(8):e198. 22 pages.
Falciatore et al., "The evolution and function of blue and red light photoreceptors." Curr Top Dev Biol. 2005;68:317-50.
Foster et al., "Extraretinal photoreceptors and their regulation of temporal physiology." Rev Reprod. Sep. 1998;3(3):145-50.
Fridovich "Oxygen: how do we stand it?. " Med Princ Pract. 2013;22(2):131-7.
Gong et al., "The C. elegans Taste Receptor Homolog LITE-1 Is a Photoreceptor." Cell. Nov. 17, 2016;167(5):1252-1263.
Haggins "Purification and partial characterization of the protein component of squid rhodopsin." J Biol Chem. May 10, 1973;248(9):3298-304.
Hu et al., "Visualization of interactions among bZIP and Rel family proteins in living cells using bimolecular fluorescence complementation." Mol Cell. Apr. 2002;9(4):789-98.
Hubbard "Absorption spectrum of rhodopsin: 500 nm absorption band." Nature. Feb. 1, 1969;221(5179):432-5.
International Search Report of related PCT/US2017/061305, mailed Feb. 13, 2018, 9 pages.
Li et al., "Encoding of both analog- and digital-like behavioral outputs by one C. elegans interneuron." Cell. Nov. 6, 2014;159(4):751-65.
Liu et al., "C. elegans phototransduction requires a G protein-dependent cGMP pathway and a taste receptor homolog." Nat Neurosci. Jun. 2010;13(6):715-22.
Maglova, L., et al. "A calorimetric study of white and purple membranes." Biochimica et biophysica acta 975 (1989): 217-220.
Marti et al., "The retinylidene Schiff base counterion in bacteriorhodopsin." J Biol Chem. Oct. 5, 1991;266(28):18674-83.

(Continued)

*Primary Examiner* — Amber D Steele
(74) *Attorney, Agent, or Firm* — Casimir Jones, S.C.; Tanya A. Arenson

(57) ABSTRACT

The present disclosure relates to compositions capable of absorbing UVA and UVB light. In particle, the present disclosure relates to UV screening compositions comprising at least a portion of LITE-1 polypeptides which are capable of absorbing UV light (e.g., UV-A and/or UV-B light).

19 Claims, 20 Drawing Sheets

Specification includes a Sequence Listing.

(56) References Cited

OTHER PUBLICATIONS

Moore et al., "UVB radiation generates sunburn pain and affects skin by activating epidermal TRPV4 ion channels and triggering endothelin-1 signaling." Proc Natl Acad Sci U S A. Aug. 20, 2013;110(34):E3225-34.
Ortiz et al., "Lateralized gustatory behavior of C. elegans is controlled by specific receptor-type guanylyl cyclases." Curr Biol. Jun. 23, 2009;19(12):996-1004.
Radding et al., "Acid-base properties of rhodopsin and opsin." J Gen Physiol. Jul. 20, 1956;39(6):909-22.
Salom et al., "Heterologous expression of functional G-protein-coupled receptors in Caenorhabditis elegans." FASEB J. Feb. 2012;26(2):492-502.
Wang et al., "Phototransduction and retinal degeneration in *Drosophila*." Pflugers Arch. Aug. 2007;454(5):821-47.
Wang et al., "The SOL-2/Neto auxiliary protein modulates the function of AMPA-subtype ionotropic glutamate receptors." Neuron. Sep. 6, 2012;75(5):838-50.
Ward et al., "Light-sensitive neurons and channels mediate phototaxis in C. elegans." Nat Neurosci. Aug. 2008;11(8):916-22.
Xiang et al., "Light-avoidance-mediating photoreceptors tile the *Drosophila* larval body wall." Nature. Dec. 16, 2010;468(7326):921-6.
Xiao et al., "A genetic program promotes C. elegans longevity at cold temperatures via a thermosensitive TRP channel." Cell. Feb. 14, 2013;152(4):806-17.
Yau et al., "Phototransduction motifs and variations." Cell. Oct. 16, 2009;139(2):246-64.
Zhang et al., "Topological and functional characterization of an insect gustatory receptor." PLoS One. 2011;6(8):e24111.

\* cited by examiner

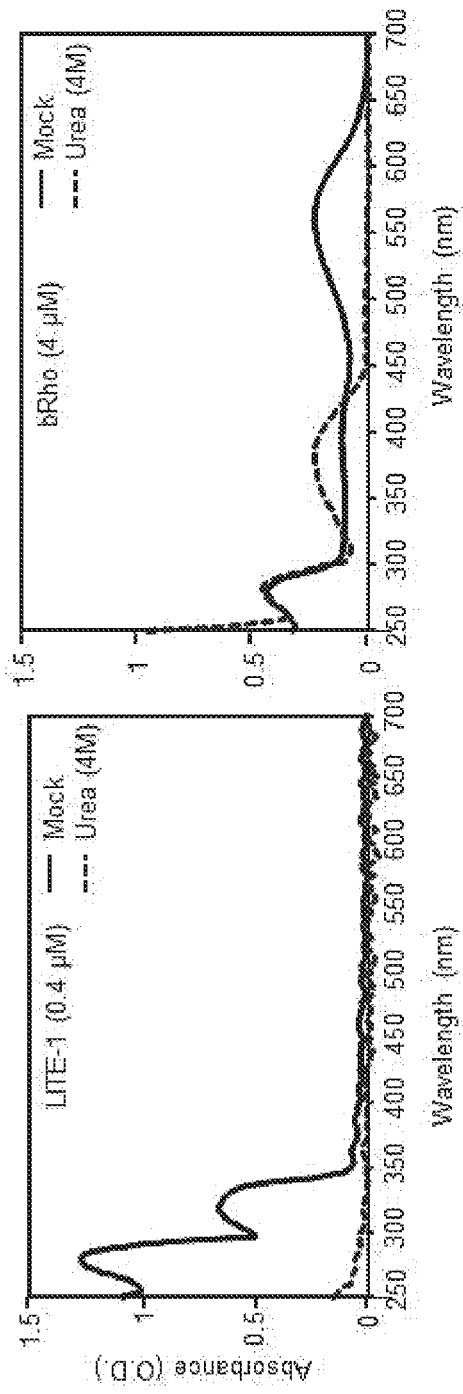
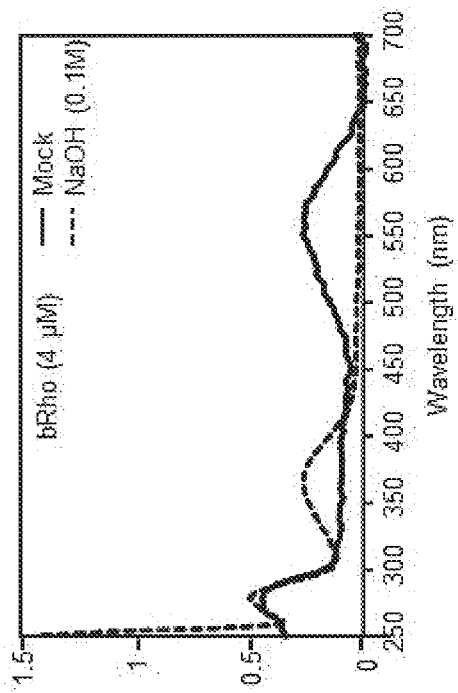
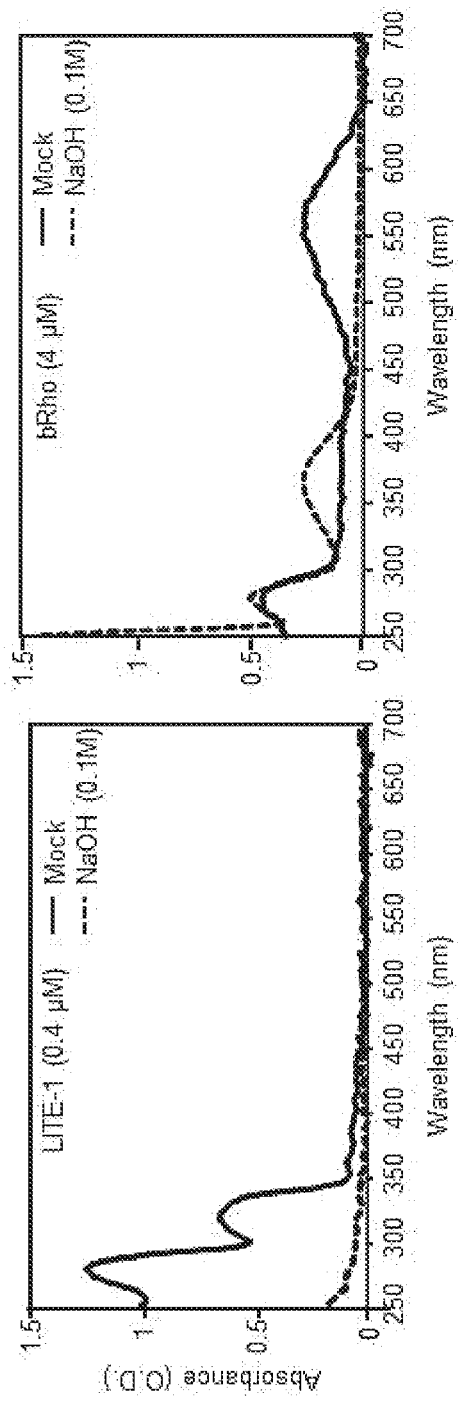
FIG.3A  FIG.3B  FIG.3C  FIG.3D

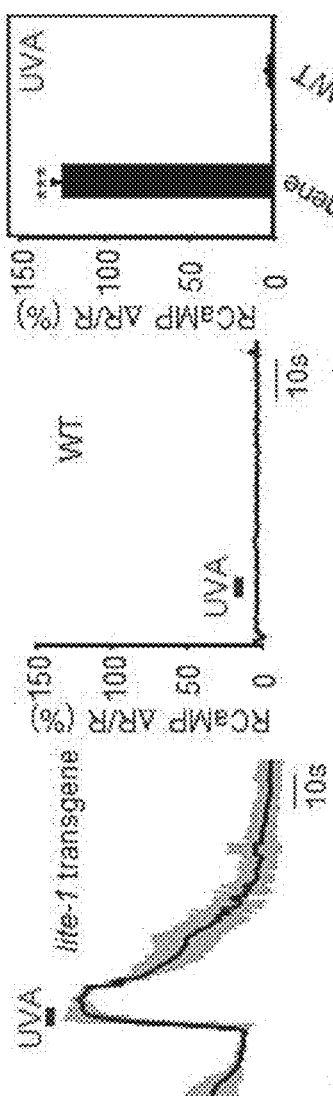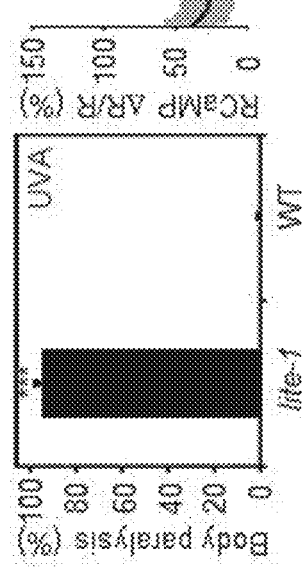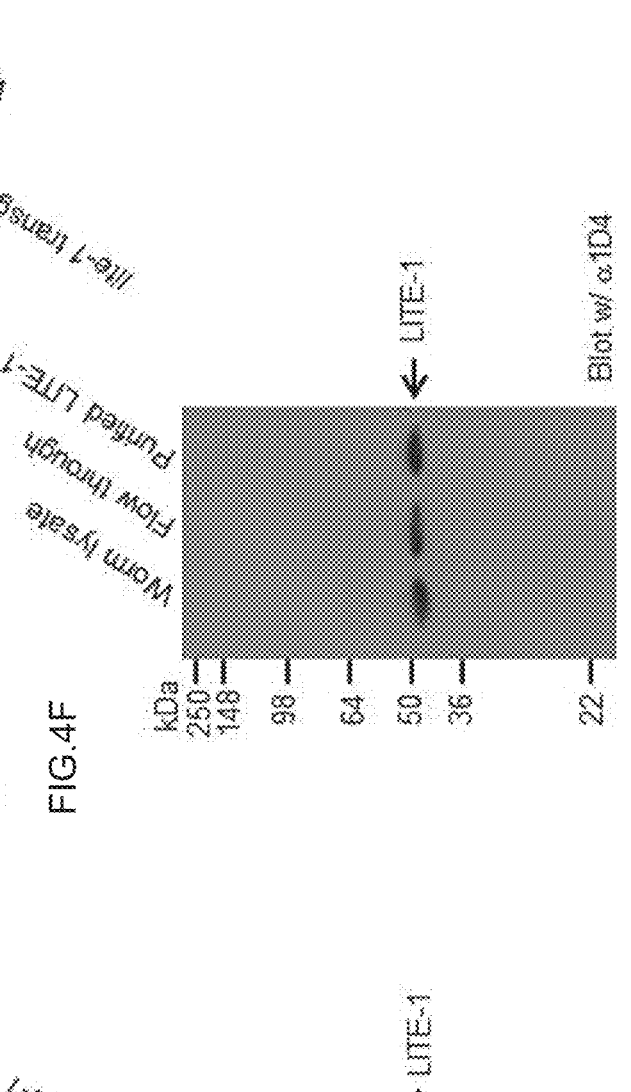
FIG. 4A  FIG. 4B  FIG. 4C  FIG. 4D  FIG. 4E  FIG. 4F

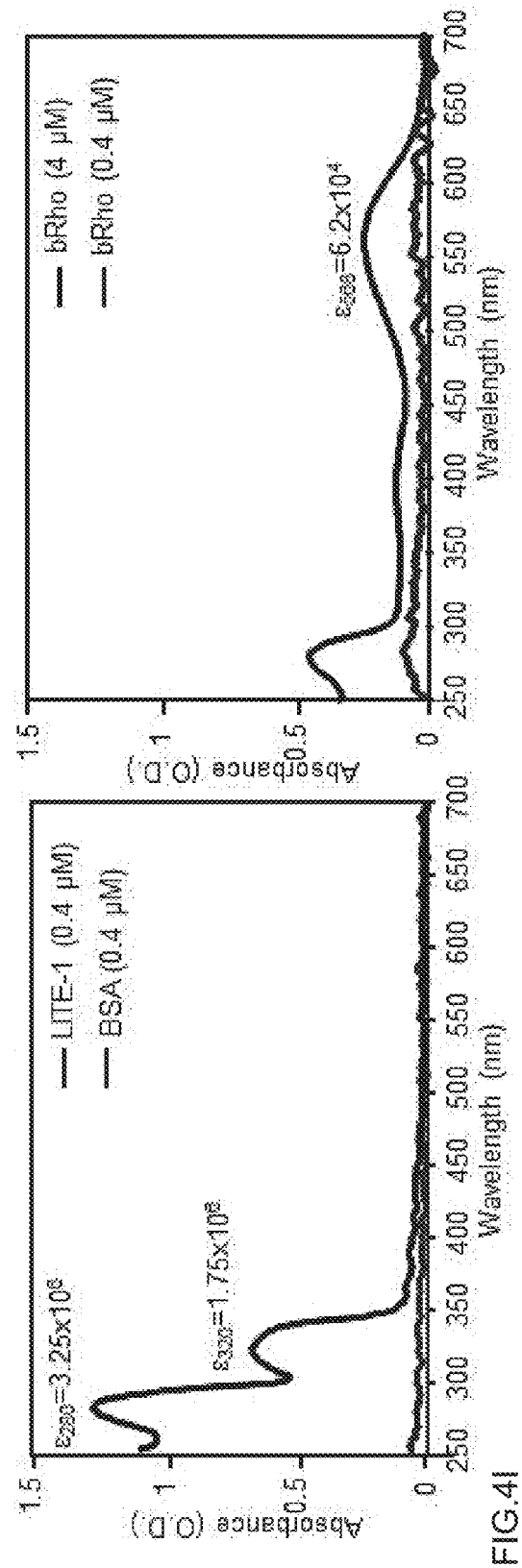
FIG. 4G
FIG. 4I
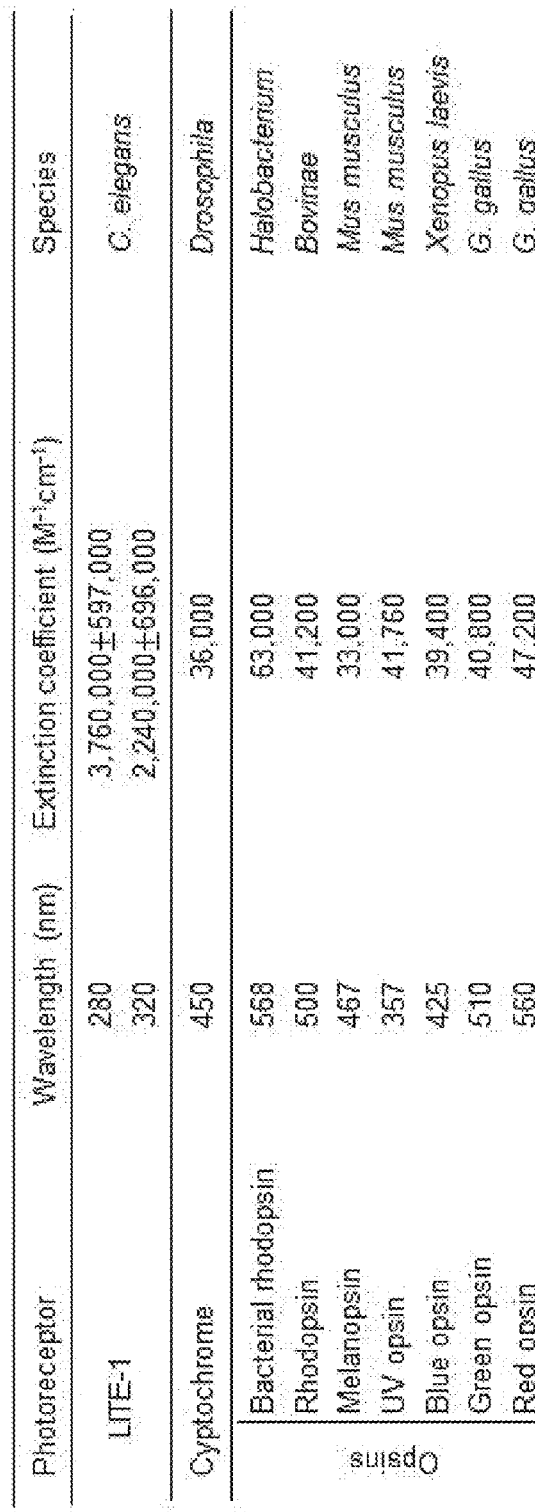
FIG. 4H
| Photoreceptor | | Wavelength (nm) | Extinction coefficient ($M^{-1}cm^{-1}$) | Species |
|---|---|---|---|---|
| LITE-1 | | 280 | 3,760,000±597,000 | C. elegans |
| | | 320 | 2,240,000±696,000 | |
| Cryptochrome | | 450 | 36,000 | Drosophila |
| Opsins | Bacterial rhodopsin | 568 | 63,000 | Halobacterium |
| | Rhodopsin | 500 | 41,200 | Bovinae |
| | Melanopsin | 467 | 33,000 | Mus musculus |
| | UV opsin | 357 | 41,760 | Mus musculus |
| | Blue opsin | 425 | 39,400 | Xenopus laevis |
| | Green opsin | 510 | 40,800 | G. gallus |
| | Red opsin | 560 | 47,200 | G. gallus |

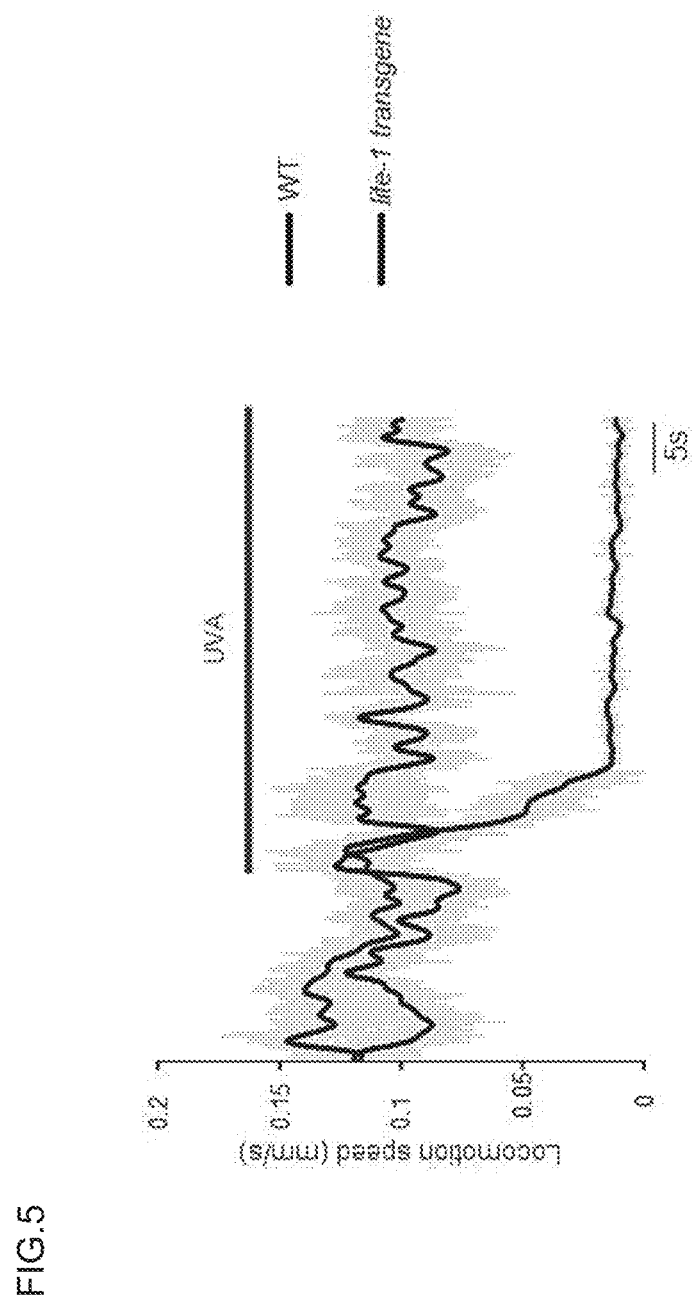
FIG.5
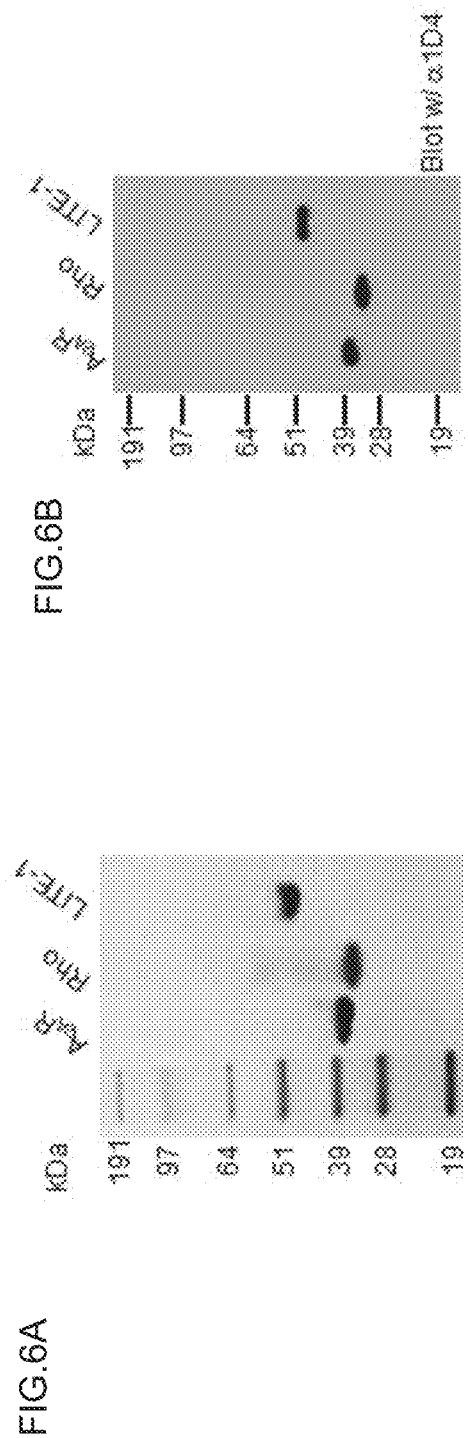
FIG.6A
FIG.6B

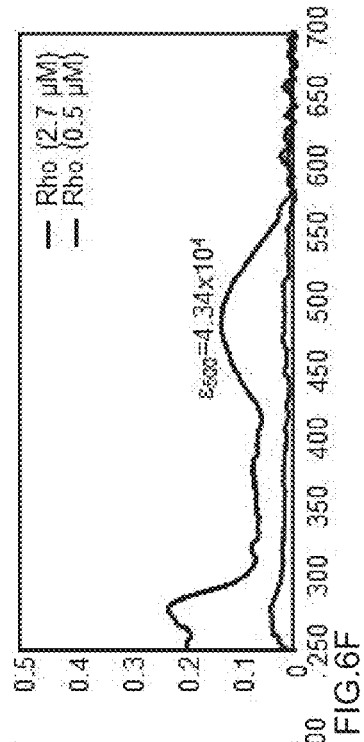 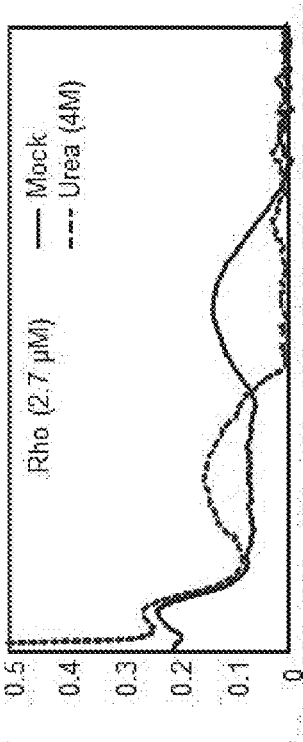 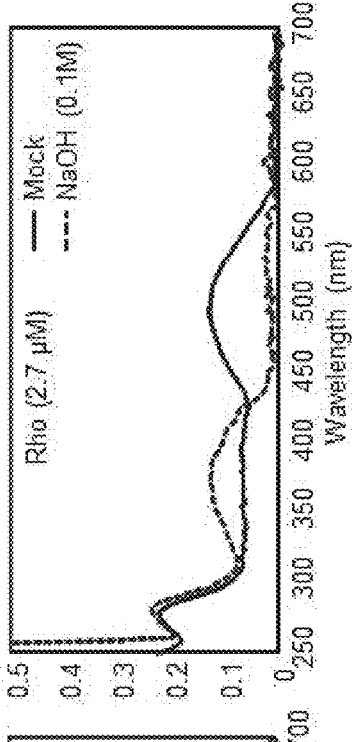
FIG.6C  FIG.6D
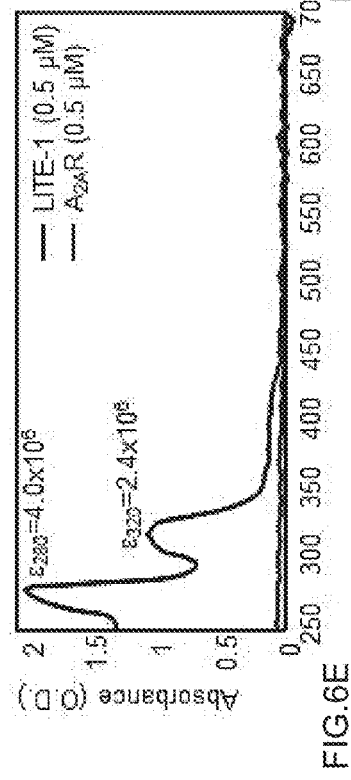 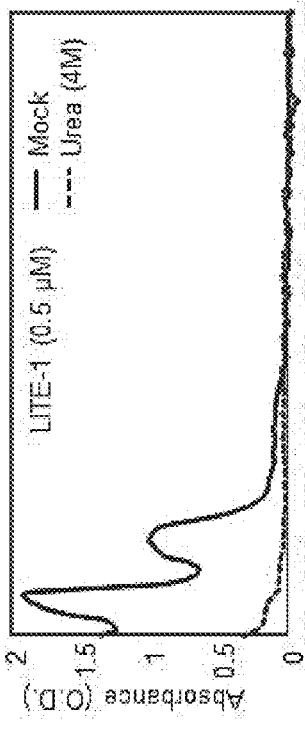
FIG.6E  FIG.6F
FIG.6G  FIG.6H

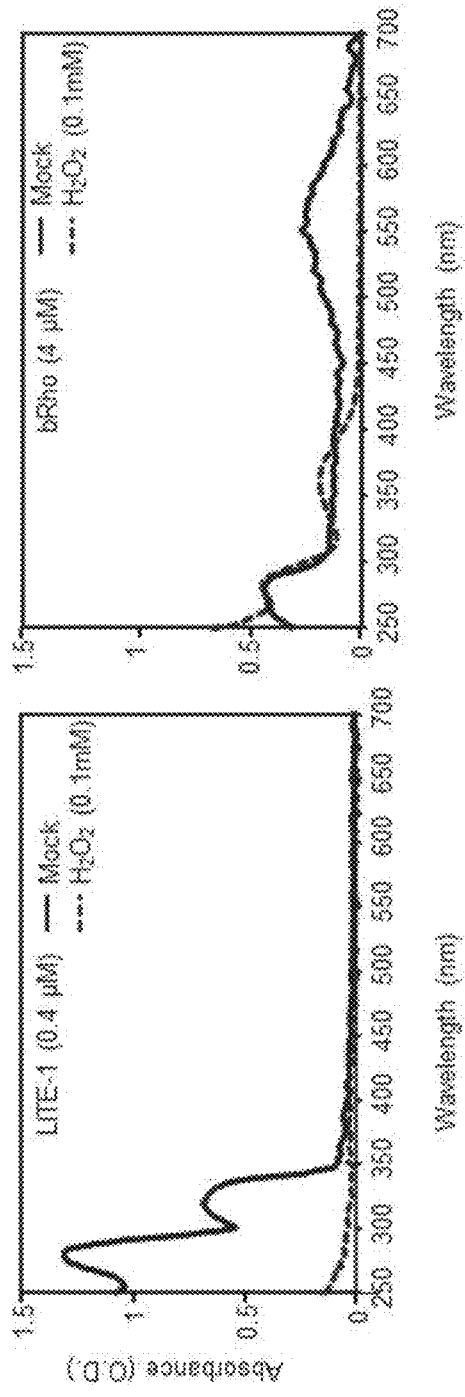
FIG. 7A
FIG. 7B
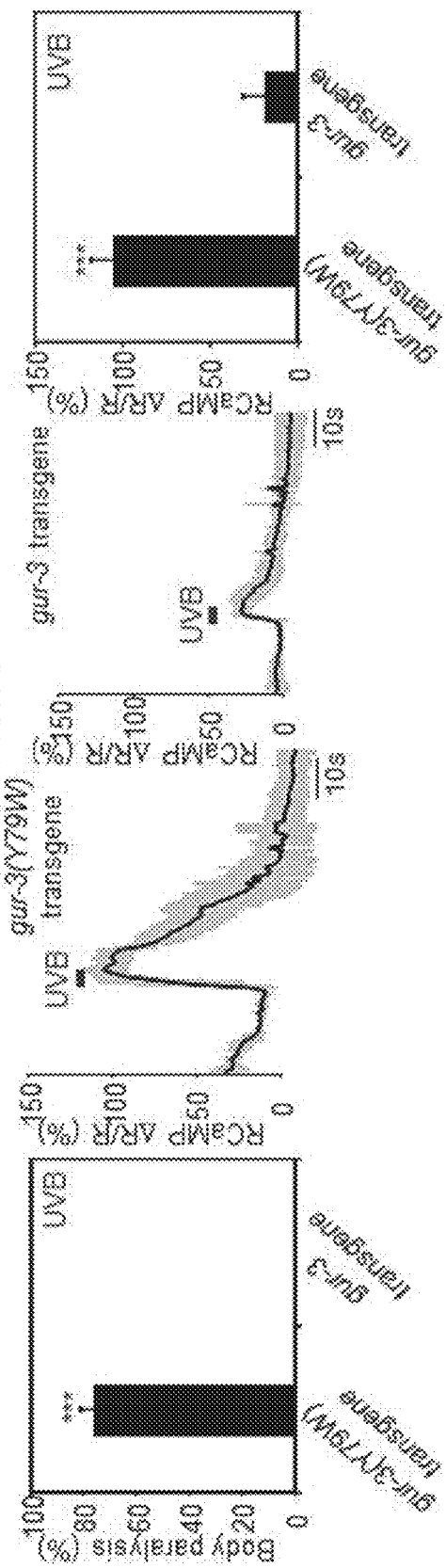
FIG. 8A
FIG. 8B
FIG. 8C
FIG. 8D

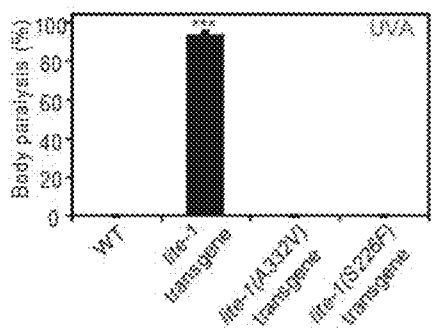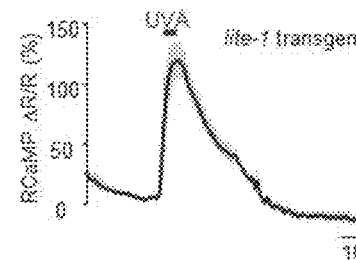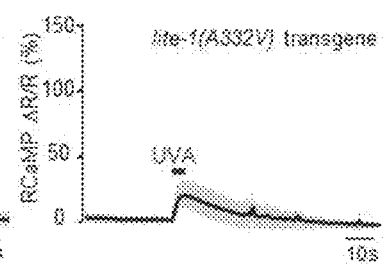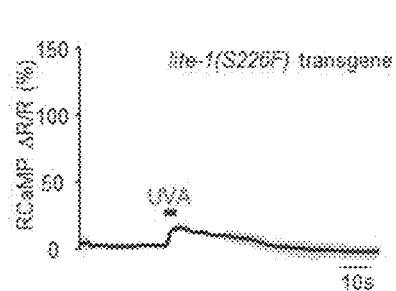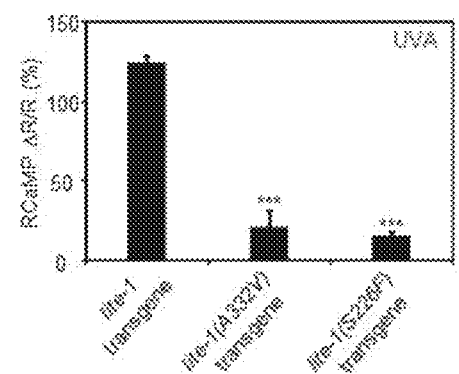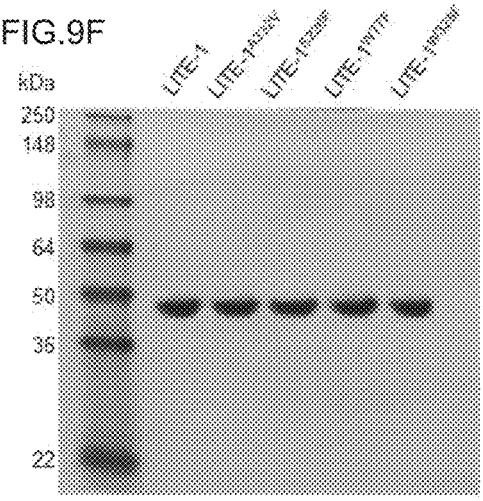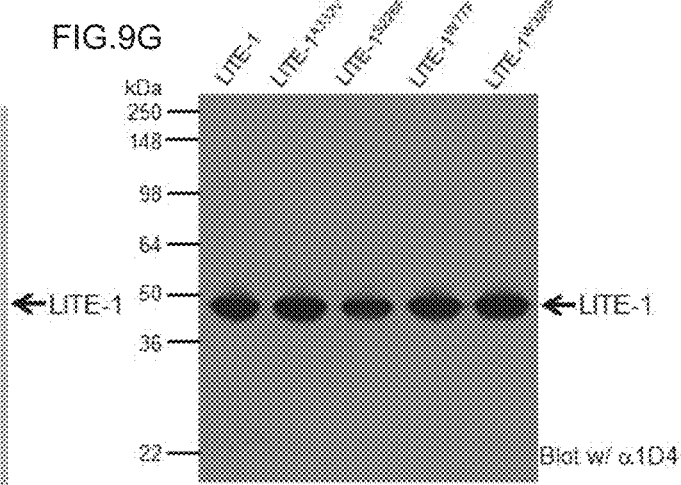

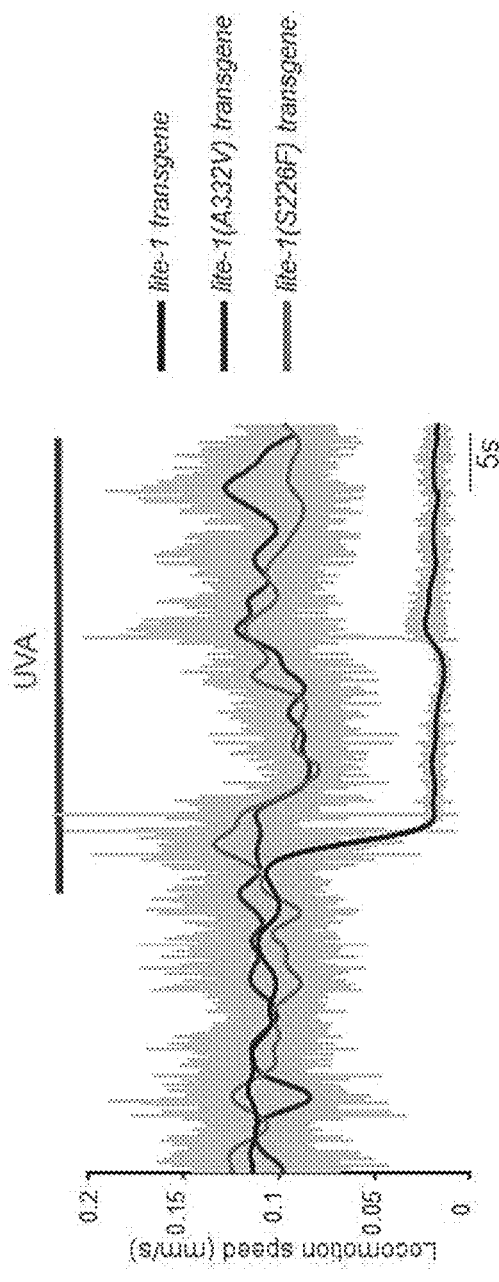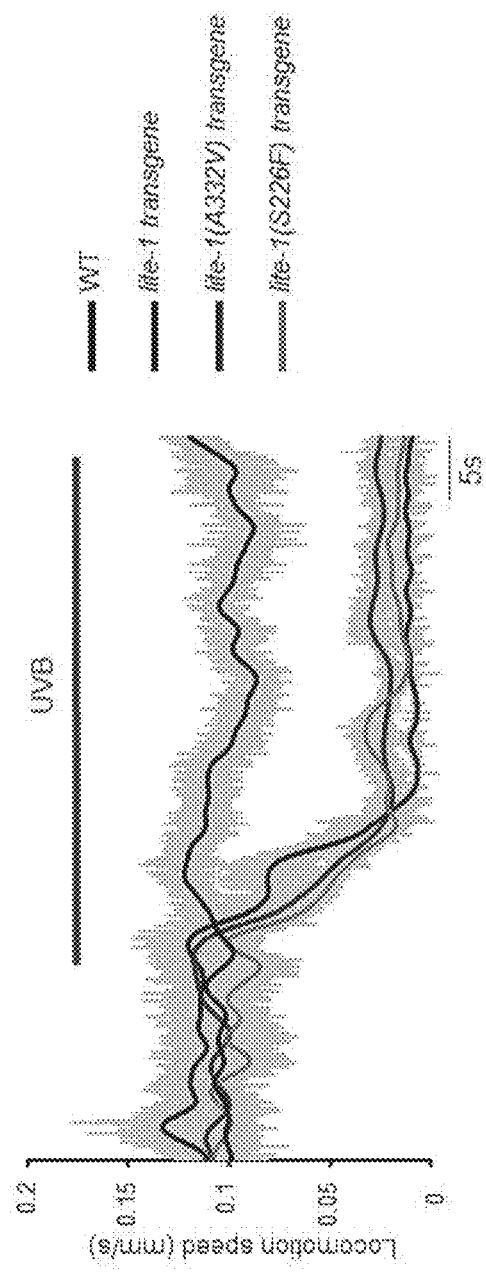

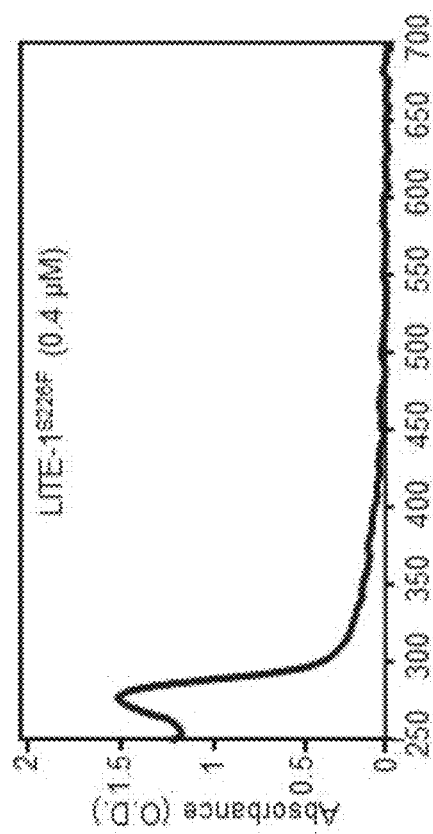
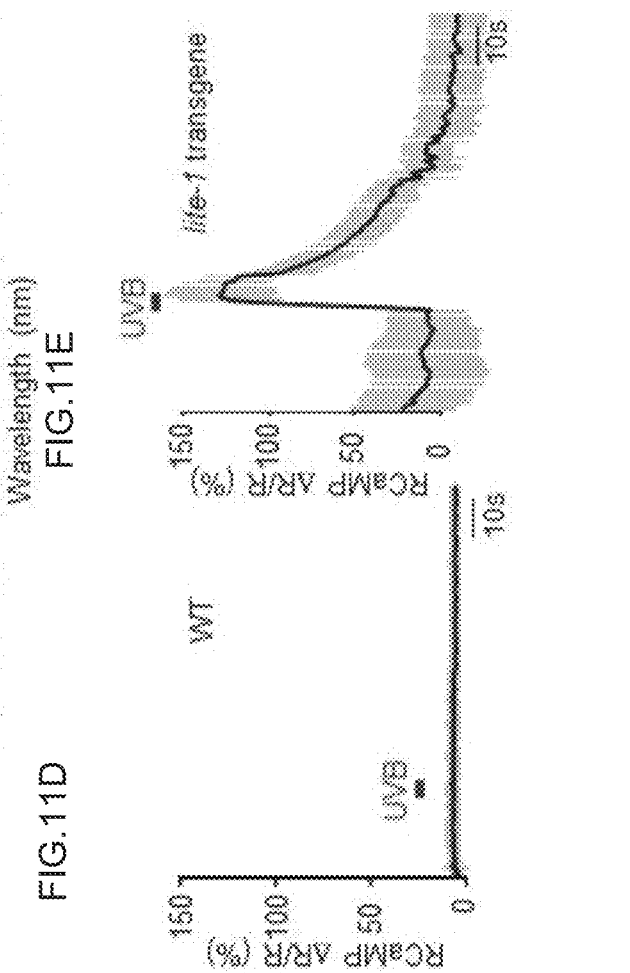
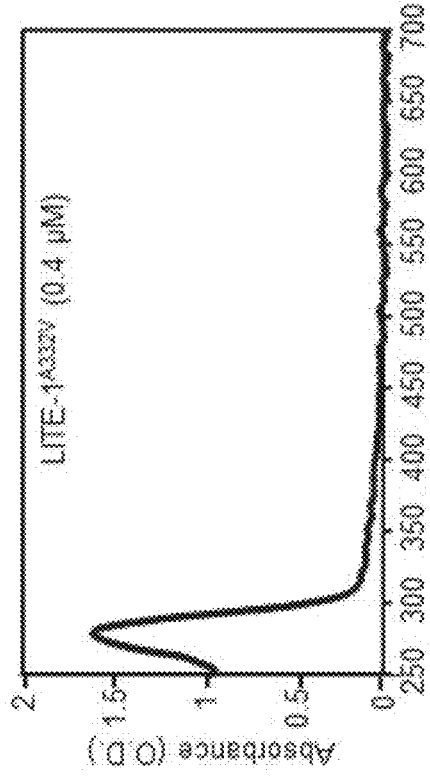
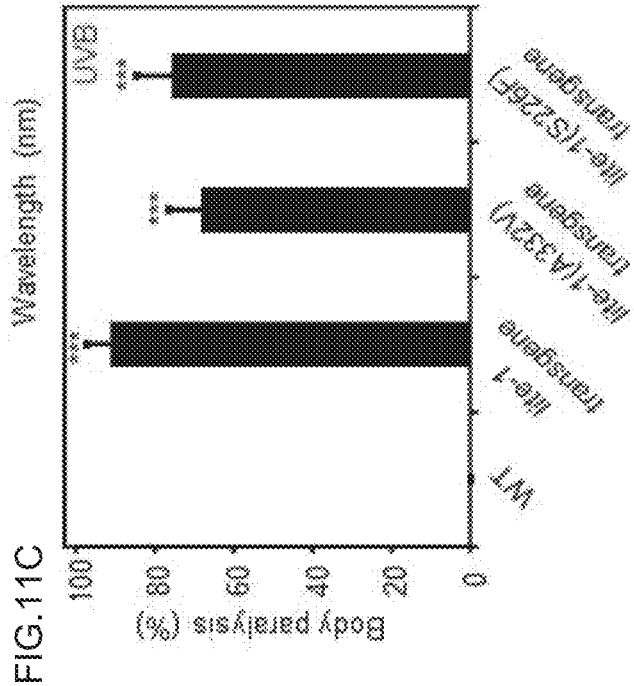
FIG.11A  FIG.11B  FIG.11C  FIG.11D  FIG.11E

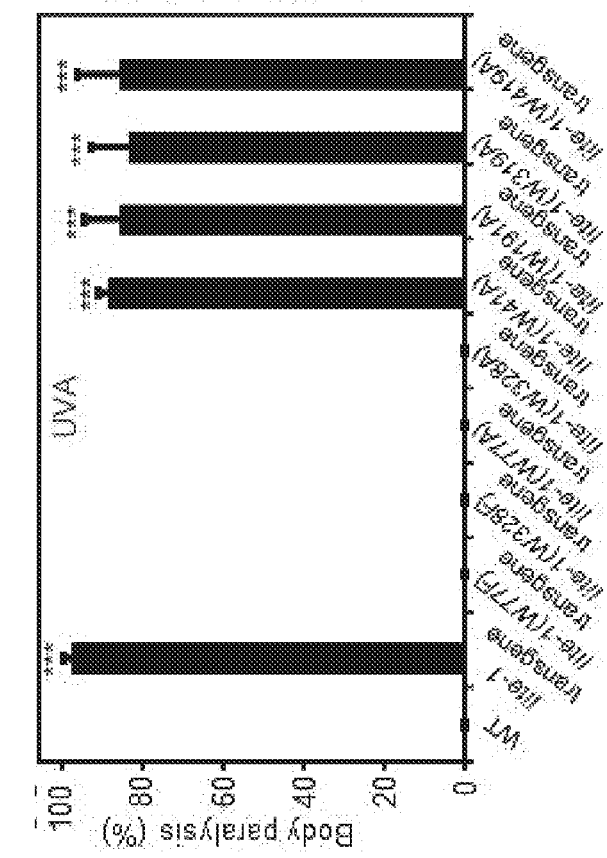
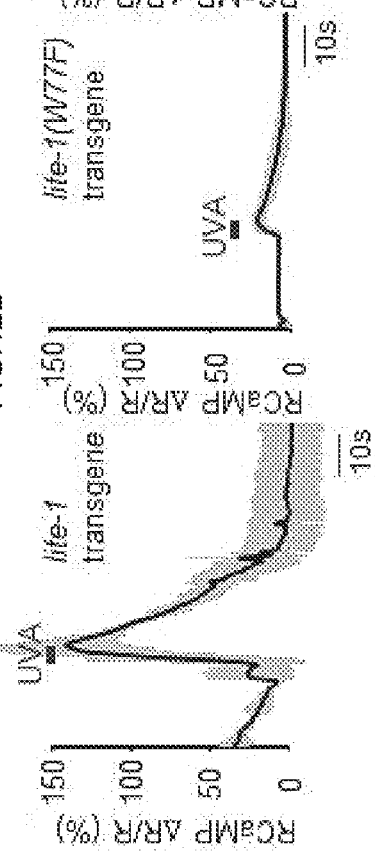
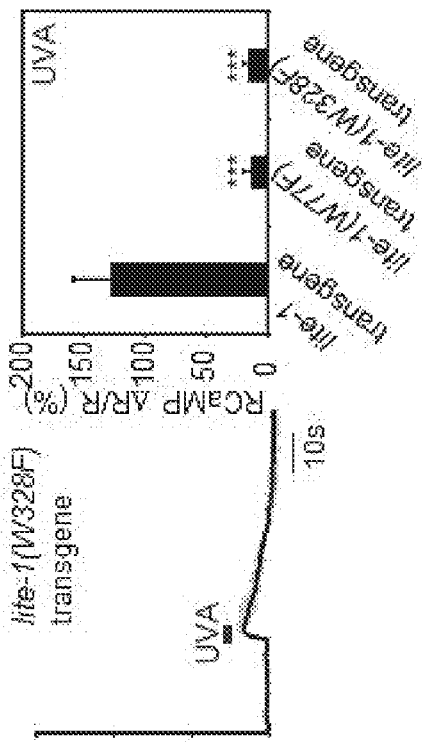
FIG. 12A
FIG. 12B
FIG. 12C
FIG. 12D
FIG. 12E
FIG. 12F

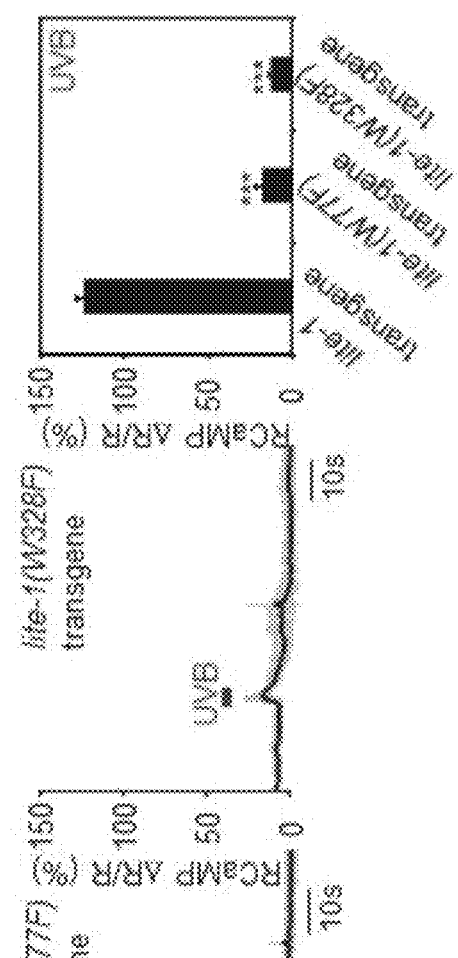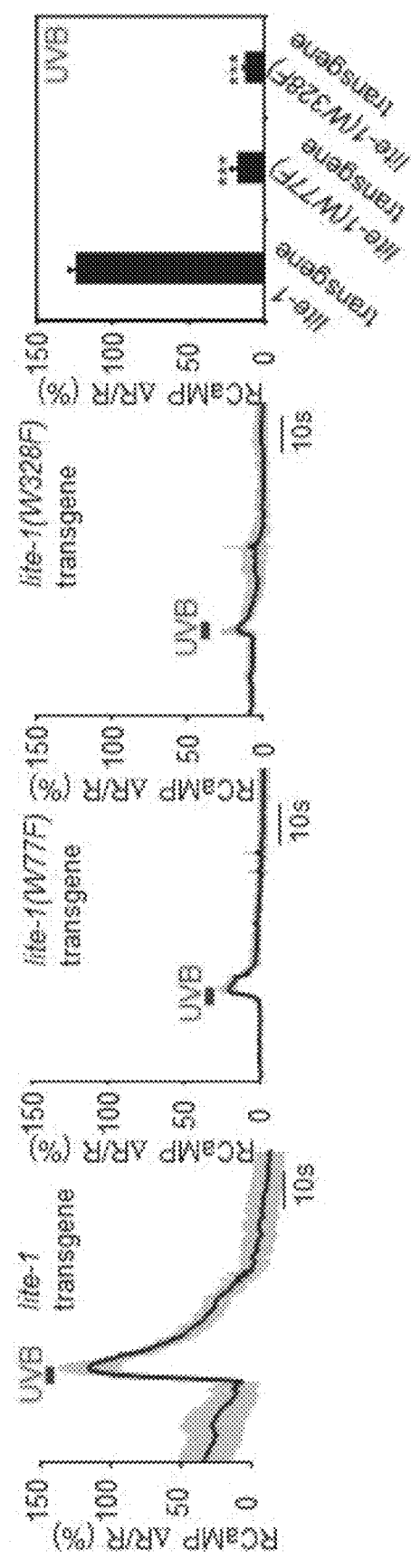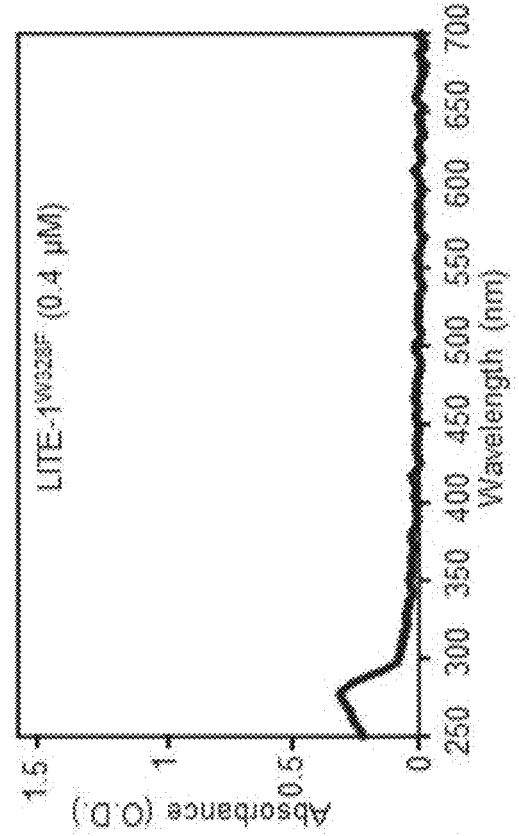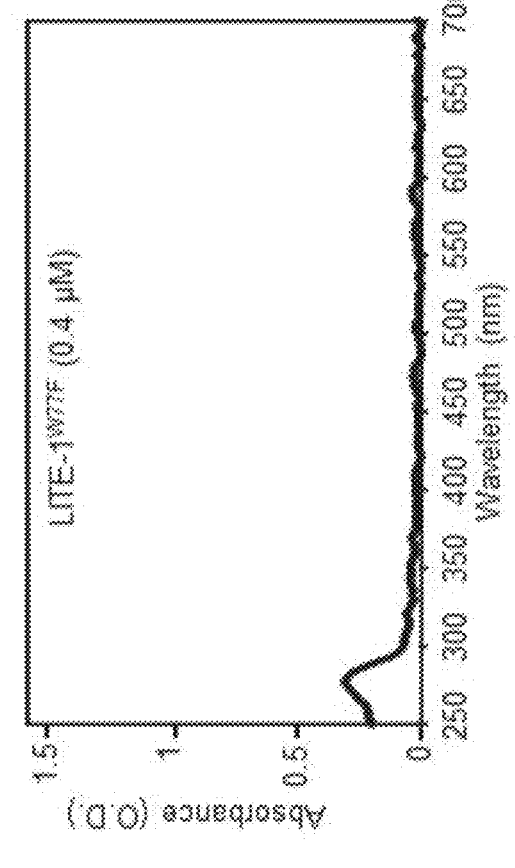

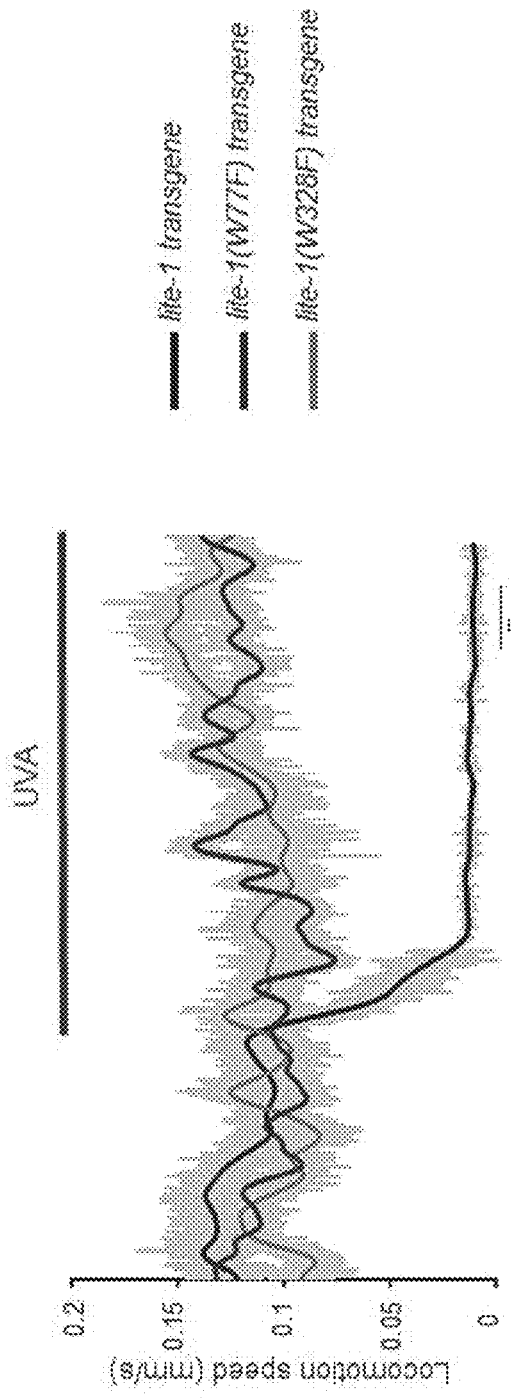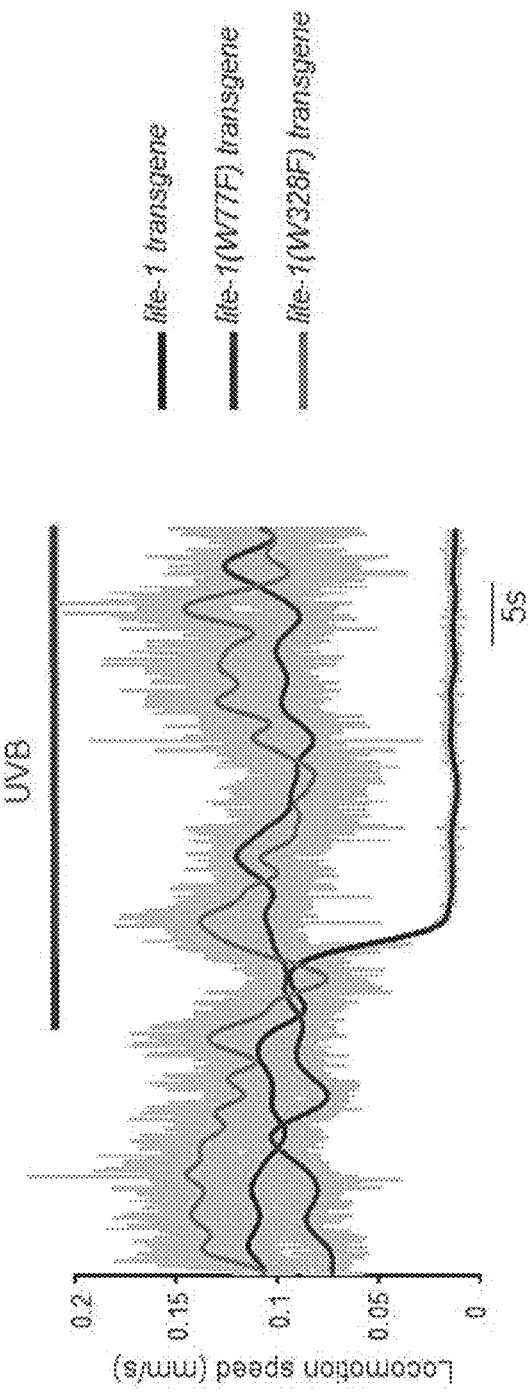
FIG.13A
FIG.13B

FIG.14

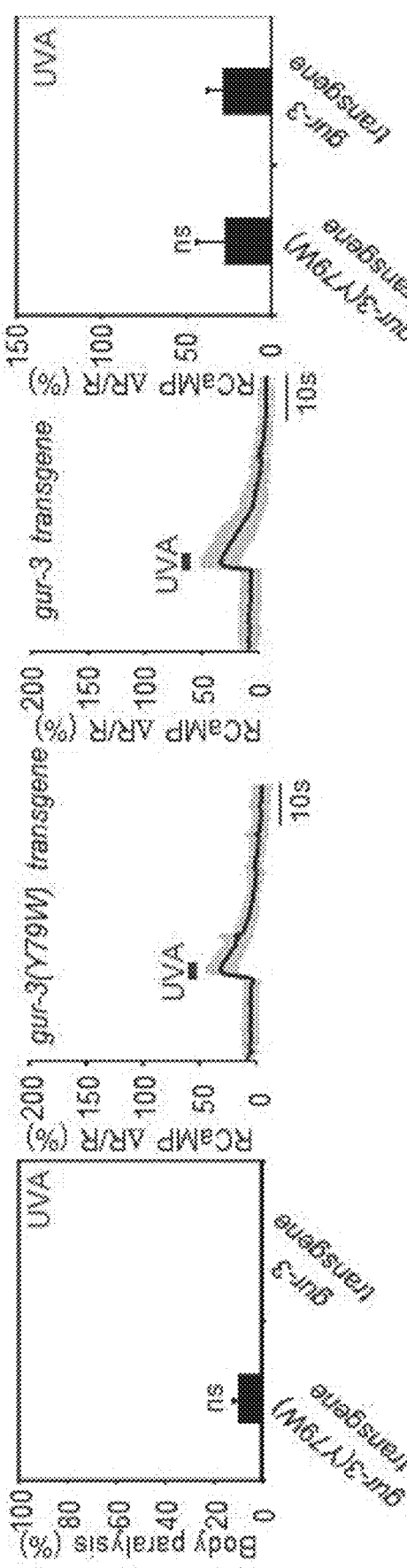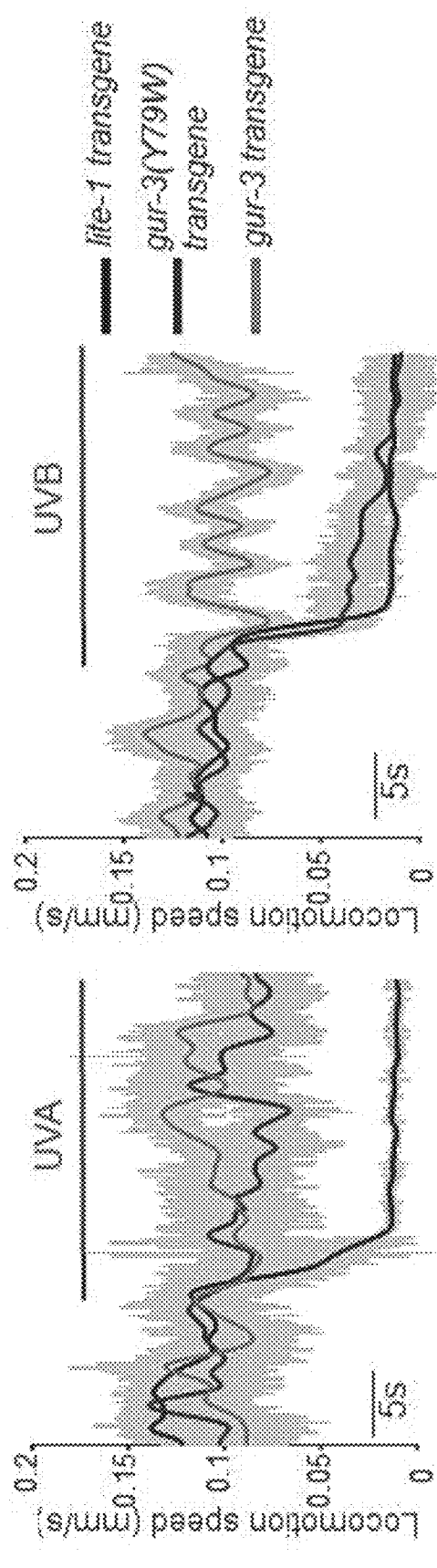

FIG.16

```
  1 mpppsshsni fhstfkhtvk etmanakktm lakilssrnk waicdrtlyp iyyllilgl
 61 nqsirpnsl lfriyswivf clilfttlrk fngvgvrpng trenigeffa nprsmiticn
121 alimisglla siqlytigak rikplkilcq fsinvrtkga errqfmintf lavfsgllal
181 tmaatyamsk wgyilyivgt pnidtetifc vildsyalfv sraaisalai ifyqhcsvir
241 rsikhlinem vpaegdecpl pesslqkihd cqisyqrifn gkavieeyys fvifysygvc
301 ipllfcflmfv qmsaqsicws evvsiviwiv nailvlllfs lpafminedg drlvassfrm
361 yhetfheerd itvlsqmtff tfqihstkit lsacnyfymd rsilislfsa iltyfliliwe
421 fdiknnqsig nianhtiht
```

FIG.17

MTITASNTLEFKWTSPRSSRSSFRTTFDAEQKISIDMSNTYCDQVLGPLYSYMMVLGLNHTHSSARNTMFKWPLTIYNYLTLAITTAATIRRISQIKQKSATNEEKDAAFHVLNPT
FVLTLCHALLMFSGLAAGFLLLKLQFQREKMYHVLDQGLGRNRNEEHDSRRFKLNKLFTSISFSFAAALSFVQIATKMRYLDLPDTPDLINRKIYFVTLEGYVIFIASSCISLVAI
LFFQLCRILQFSIGQLIEEMVPKEKEECPLPEQSLQQIHDVQIHYQEISNAKLYIEQNFSFSLFYTGCCIPTCLLGYIAFRNGIQADMAETFSVAIWLTNTMLALMLFSIPAFM
IAEEGDKLLTASFKMYHETLCEERDLLVLSQMSFLSFQMHATKLTLAGNFFMMNRKIMISLFSAIFTYFLLVQFDAEKERAGECNNQSRVLIVQPPV

SEQUENCE LISTING

```
Sequence total quantity: 7
SEQ ID NO: 1            moltype = AA  length = 439
FEATURE                 Location/Qualifiers
source                  1..439
                        mol_type = protein
                        organism = Caenorhabditis elegans
SEQUENCE: 1
MPPPSSHSNI FHSTFKHTVK ETMANAKKTM IAKILSSRNK WAICDRTLYP IYYLLLILGL   60
NQSIRPNNSL LFRIYSWLVF CLLLFTTLRK FNQVGVRPNG TRENLQEFFA NPRSMITLCN  120
ALIMLSGLLA SLQLYTLGAK RLKPLKILCQ FSLNVRTKQA ERRQFMINTF LAVFSGLLAL  180
TMAATYAMSK WGYILYIVGT PNLDTETIFC VLLDSYALFV SRAAISALAI LFYQHCSVIR  240
RSIKHLINEM VPAEQDECPL PESSLQKIHD CQISYQRIFN GKAVIEEYYS FVLFYSYGVC  300
IPIFCFLMFV GMSAQSICWS EVVSIVIWIV NAILVLLLFS LPAFMINEDG DRLVASSFRM  360
YHETFHEERD LTVLSQMTFF TFQIHSTKLT LSACNYFYMD RSILLSLFSA ILTYFLILWE  420
FDIKNNQSLQ NIANHTIHT                                               439

SEQ ID NO: 2            moltype = AA  length = 447
FEATURE                 Location/Qualifiers
source                  1..447
                        mol_type = protein
                        organism = Caenorhabditis elegans
SEQUENCE: 2
MTITASNTLE FKWTSPRSSR SSFRTTTDAE QKISIDMSNT YCDQVLGPLY SYMMVLGLNH   60
THSSARNTMF KWPLTIYNYL TLAILTAATI RRISQIKQKS ATNEEKDAAF HVLNPTFVLT  120
LCHALLMFSG LAAGFLLLKL QKQREKMYHV LDQGLGRNRN EEHDSHHFKL NKLFISISFS  180
FAAALSFVQI ATKMRYLDLP DTPDLINRKI YFVILEGYVI FIASSCISLV AILFFQLCRI  240
LQFSIGQLIE EMVPKEKEEC PLPEQSLQQI HDVQIHYQEI SNAKLYIEQN FSFSLFYTYG  300
CCIPLTCLLG YIAFRNGIQA DMAETFSVAI WLTNTMLALM LFSIPAFMIA EEGDKLLTAS  360
FKMYHETLCE ERDLLVLSQM SFLSFQMHAT KLTLTAGNFF MMNRKIMISL FSAIFTYFLI  420
LVQFDAEKER AGECNNQSRV LIVQPPV                                      447

SEQ ID NO: 3            moltype = AA  length = 72
FEATURE                 Location/Qualifiers
source                  1..72
                        mol_type = protein
                        organism = Caenorhabditis elegans
SEQUENCE: 3
IYSWLVFCLL LFTTLRKFNQ VGVRPNGTRE NLQEFFANAQ SICWSEVVSI VIWIVNAILV   60
LLLFSLPAFM IN                                                      72

SEQ ID NO: 4            moltype = AA  length = 75
FEATURE                 Location/Qualifiers
source                  1..75
                        mol_type = protein
                        organism = Caenorhabditis elegans
SEQUENCE: 4
IYNYLTLAIL TAATIRRISQ IKQKSATNEE KDAAFHVLNN GIQADMAETF SVAIWLTNTM   60
LALMLFSWIP AFMIA                                                   75

SEQ ID NO: 5            moltype = AA  length = 65
```

```
FEATURE            Location/Qualifiers
source             1..65
                   mol_type = protein
                   organism = Caenorhabditis elegans
SEQUENCE: 5
LFLFRLLAIF PATTDRKSRR KRNHRSIIKL ILYVNVHVKI CWAAYQVVMA ILHIIIICST    60
GMMTN                                                                65

SEQ ID NO: 6       moltype = AA  length = 35
FEATURE            Location/Qualifiers
source             1..35
                   mol_type = protein
                   organism = Caenorhabditis elegans
SEQUENCE: 6
LRIDLRKPQA KRNINYDLIL CMPTIGLCAF SFFAV                                35

SEQ ID NO: 7       moltype = AA  length = 36
FEATURE            Location/Qualifiers
source             1..36
                   mol_type = protein
                   organism = Caenorhabditis elegans
SEQUENCE: 7
LRLDFVNSDQ WARKINTDFL ICMPFILFCT CAFCSV                               36
```

COMPOSITIONS AND METHODS FOR BLOCKING ULTRAVIOLET RADIATION

CROSS-REFERENCE TO RELATED APPLICATIONS

This application is a continuation of U.S. application Ser. No. 17/122,358, filed Dec. 15, 2020, now U.S. Pat. No. 11,744,790, which is a continuation of U.S. application Ser. No. 16/349,448, filed May 13, 2019, now U.S. patent application Ser. No. 10,864,153, issued Dec. 15, 2020, which is a national phase application under 35 U.S.C. § 371 of PCT International Application No. PCT/US2017/061305, filed Nov. 13, 2017, which claims the benefit of U.S. provisional application Ser. No. 62/421,672, filed Nov. 14, 2016, the disclosure of which are incorporated herein by reference in their entireties.

STATEMENT REGARDING FEDERALLY SPONSORED RESEARCH OR DEVELOPMENT

This invention was made with government support under EY022315 and GM083241 awarded by the National Institutes of Health. The government has certain rights in the invention.

SEQUENCE LISTING

The text of the computer readable sequence listing filed herewith, titled "UM-35075-304_SQL", created Feb. 16, 2023, having a file size of 8,273 bytes, is hereby incorporated by reference in its entirety.

FIELD OF THE DISCLOSURE

The present disclosure relates to compositions capable of absorbing UVA and UVB light. In particular, the present disclosure relates to UV screening compositions comprising at least a portion of LITE-1 polypeptides which are capable of absorbing UV light (e.g., UV-A and/or UV-B light).

BACKGROUND OF THE DISCLOSURE

The harmful effects from exposure to ultraviolet (UV) radiation can be classified as acute or chronic. The acute effects of UV-A and UV-B exposure are both short-lived and reversible. These effects include mainly sunburn (or erythema) and tanning (or pigment darkening). The chronic effects of UV exposure can be much more serious, even life threatening, and include premature aging of the skin, suppression of the immune system, damage to the eyes, and skin cancer.

According to the National Toxicology Program Report on Carcinogens from the US Department of Health and Human Services, broad-spectrum UV radiation is a carcinogen whose DNA damage is thought to contribute to most of the estimated 1.5 million skin cancers and the 8,000 deaths due to metastatic melanoma that occur annually in the United States.

Despite the importance of the sun to vitamin D synthesis, it is prudent to limit the exposure of skin to UV radiation from sunlight and from tanning beds. The American Academy of Dermatology advises that photoprotective measures be taken, including the use of sunscreen, whenever one is exposed to the sun. Short-term over-exposure causes the pain and itching of sunburn, which in extreme cases can produce more-severe effects like blistering.

Additional compositions and methods for preventing UV light damage are needed.

SUMMARY

Many animal tissues/cells are photosensitive, yet only two types of photoreceptors (opsins and cryptochromes) have been discovered in metazoans. The question arises as to whether unknown types of photoreceptors exist in the animal kingdom. LITE-1, a seven-transmembrane gustatory receptor (GR) homolog, mediates UV light-induced avoidance behavior in C. elegans. However, it remains unclear whether LITE-1 functions as a chemoreceptor or photoreceptor. Experiments conducted during the course of developing embodiments for the present disclosure determined that LITE-1 directly absorbs both UVA and UVB light with an extinction coefficient 10-100 times that of opsins and cryptochromes, indicating that LITE-1 is highly efficient in capturing photons. Unlike typical photoreceptor proteins employing a prosthetic chromophore to capture photons, LITE-1 strictly depends on its protein conformation for photon absorption. Such experiments further identified two tryptophan residues critical for LITE-1 function. Interestingly, unlike GPCRs, LITE-1 adopts a reversed membrane topology. Thus, LITE-1, a taste receptor homolog, represents a distinct type of photoreceptor in the animal kingdom.

Accordingly, the present disclosure relates to compositions capable of absorbing UVA and UVB light. In particular, the present disclosure relates to UV screening compositions comprising at least a portion of LITE-1 and/or GUR-3 polypeptides which are capable of absorbing UV light (e.g., UV-A and/or UV-B light).

For example, in some embodiments, in some embodiments, the present disclosure provides a composition, comprising: a) an LITE-1 polypeptide or fragment, portion, or mimetic thereof; and b) at least one carrier. The present disclosure is not limited to particular LITE polypeptides. In some embodiments, the LITE-1 is wild type C. elegans LITE-1 (e.g., SEQ ID NO:1 or sequences at least 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:1). In some embodiments, the LITE-1 peptide is isolated from C. elegans, recombinant, or synthesized. In some embodiments, the LITE-1 polypeptide comprises one or more mutations. In some embodiments, the mutations are not W77 or W328. In some embodiments, the GUR-3 polypeptide is wild type C. elegans GUR-3 (e.g., SEQ ID NO:2 or sequences at least 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:2). In some embodiments, the GUR-3 polypeptide comprises one or more mutations (e.g., Y79W). In some embodiments, the LITE-1 or GUR-3 polypeptide absorbs UVA and/or UVB light. In some embodiments, the carrier is a pharmaceutically acceptable carrier. The present disclosure is not limited to a particular carrier. In some embodiments, the carrier comprises one or more carriers selected from, for example, preservatives, emollients, emulsifying agents, surfactants, moisturizers, gelling agents, thickening agents, conditioning agents, film-forming agents, stabilizing agents, anti-oxidants, texturizing agents, gloss agents, mattifying agents, solubilizers, pigments, dyes, or fragrances. In some embodiments, the composition is a pharmaceutical composition, a cosmetic composition, a sunscreen, an aerosol, a moisturizer, a gel, an ointment, a stick, a cream, or a lotion. In some embodiments, composition is formulated for topical administration.

In further embodiments, the composition is formulated for industrial use. For example, in some embodiments, the present disclosure provides films, lenses, structural elements, or coatings comprising LITE-1 and/or GUR-3 polypeptides. In some embodiments, the carrier is a polymer or plastic.

Yet other embodiments provide a method of protecting skin against UVA and/or UVB light, comprising: contacting skin of a subject with a composition described herein.

Still other embodiments provide the use of the compositions described herein to protect skin against UVA and/or UVB light.

Additional embodiments will be apparent to persons skilled in the relevant art based on the teachings contained herein.

BRIEF DESCRIPTION OF THE DRAWINGS

FIG. 3A-D shows that photoabsorption by LITE-1 relies on its conformation. (A) Denaturing LITE-1 with urea completely abolishes its photoabsorption. Shown are spectral data for mock- and urea-treated LITE-1. (B) Denaturing bacterial rhodopsin (bRho) with urea does not eliminate its photoabsorption. (C) Denaturing LITE-1 with NaOH completely abolishes its photoabsorption. (D) Denaturing bacterial rhodopsin (bRho) with NaOH does not eliminate its photoabsorption.

FIG. 4A-I shows that LITE-1 absorbs UVA and UVB light, and ectopic expression of LITE-1 confers photosensitivity to photo-insensitive cells. (A) Transgenic expression of LITE-1 in muscle cells confers photosensitivity shown by behavioral assays. (B-D) Transgenic expression of LITE-1 in muscle cells confers photosensitivity shown by calcium imaging. Shades along the traces in (B) and (C) represent SEM. $n≥7$. (E-F) Purification of LITE-1. Shown in (E) is an SDS-PAGE gel stained with coomassie blue. Shown in (F) is a Western blot probed with anti-1D4 that recognizes the 1D4 tag attached to the C-terminal end of LITE-1. The amount of each sample loaded in (F) was 1/10 of that in (E). (G) LITE-1 shows strong absorption of UVA and UVB light while BSA does not. (I) LITE-1 is far more efficient in photon absorption than cryptochromes and opsins.

FIG. 5 shows etopic expression of LITE-1 as a transgene in muscle cells confers photosensitivity.

FIG. 6A-H shows a comparison of the spectral properties of LITE-1, bovine rhodopsin (Rho) and adenosine $A_{2A}$ receptor ($A_{2A}R$) purified from worm muscles. (A-B) LITE-1, Rho, and $A_{2A}R$ were purified side-by-side from transgenic worms under the same conditions. (A) coomassie staining. (B) Western. (C) LITE-1 shows strong photoabsorption at 0.5 mM, whereas $A_{2A}R$ does not. (D) Rho shows minimal photoabsorption at 0.5 mM, and only shows modest photoabsorption at a higher concentration (2.7 mM). Note: the Y-axis scale in (C) and (D) are different. (E-F) Denaturing LITE-1 with urea completely abolishes its photoabsorption (E), whereas the same treatment does not eliminate the photoabsorption of Rho and instead shifts its 500 nm absorbance peak to 370 nm (F). (G-H) Denaturing LITE-1 with NaOH completely abolishes its photoabsorption (E), whereas the same treatment on Rho does not and instead shifts its 500 nm absorbance peak to 370 nm (F).

FIG. 7A-B shows the impact of $H_2O_2$ on LITE-1 photoabsorption. (A) $H_2O_2$ treatment completely abolishes the light absorption of LITE-1. (B) $H_2O_2$ treatment does not abolish the photosensitivity of bacterial rhodopsin (bRho) but shifts its absorbance peak from 568 nm to 370 nm FIG. 8A-I shows genetic engineering of a photoreceptor by introducing a tryptophan residue into another GR family member GUR-3. (A) Mutating Y79 to W in GUR-3 promotes photosensitivity in vivo shown by behavioral assays. GUR-$3^{Y79W}$ and GUR-3 were expressed as a transgene in muscle cells. Worms were exposed to a 20 sec pulse of UVB light (280±10 nm, 0.03 mW/mm$^2$), and those showing muscle contraction-induced paralysis during light illumination were scored positive. n=50. Error bars: SEM. *p<0.00001 (t test). (B-D) Mutating Y79 to W in GUR-3 promotes photosensitivity in vivo shown by calcium imaging. Shades along the traces in (B-C) represent SEM. (D) Bar graph. n=20. *p<0.00001 (t test). (E-F) Purification of GUR-$3^{Y79W}$ and GUR-3. Shown in (E) is an SDS-PAGE gel stained with coomassie blue. Shown in (F) is a Western blot probed with anti-1D4 that recognizes the 1D4 tag attached to the C-terminus of GUR-$3^{Y79W}$ and GUR-3, as well as LITE-1. LITE-1 was purified side-by-side as a reference. As predicted, GUR-3 showed a slightly larger molecular weight than LITE-1. The amount of each sample loaded in (F) was 1/10 of that in (E). Samples for SDS-PAGE and Western were prepared at room temperature under non-reducing conditions (free of β-ME and DTT) to avoid aggregation of LITE-1. (G-H) Mutating Y79 to W in GUR-3 greatly potentiates the absorption of UVB light (280 nm) in vitro. (I) A schematic model denoting LITE-1 membrane topology and the position of residues investigated in this study.

FIG. 9A-G shows that residues S226 and A332 in LITE-1 are critical for its sensitivity to UVA light in vivo. (A) S226F and A332V mutations disrupt the function of LITE-1 in vivo shown by behavioral assays. (B-E) S226F and A332V mutations disrupt the function of LITE-1 in vivo shown by calcium imaging. Shades along the traces in (B-D) represent SEM. (E) Bar graph. n≥7. ***p<0.00001 (ANOVA with Bonferroni test). (F-G) Purification of mutant forms LITE-1. Shown in (E) is an SDS-PAGE gel stained with coomassie blue. Shown in (G) is a Western blot probed with anti-1D4 that recognizes the 1D4 tag attached to the C-terminus of LITE-1 variants. The amount of each sample loaded in (G) was 1/10 of that in (F).

FIG. 10A-B shows that residues S226 and A332 in LITE-1 are critical for its sensitivity to UVA but not UVB light in vivo. (A-B) LITE-$1^{S226F}$ and LITE-$1^{A332V}$ were expressed as a transgene in muscle cells under the myo-3 promoter. (B) light was directed to the worm, which induced muscle contraction, leading to paralysis of the worm (locomotion speed reduced to zero).

FIG. 11A-I shows that residues S226 and A332 in LITE-1 are required for its absorption of UVA but not UVB light in vitro. (A-B) S226F and A332V mutations disrupt LITE-1's absorption of UVA but not UVB light in vitro. (C) S226F and A332V mutations do not disrupt the sensitivity of LITE-1 to UVB light in vivo shown by behavioral assays. (D-H) S226F and A332V mutations do not disrupt the sensitivity of LITE-1 to UVB light in vivo shown by calcium imaging. Shades along the traces in (D-G) represent SEM. (H) Bar graph. n≥10. ***p<0.00001 (ANOVA with Bonferroni test). (I) LITE-1 absorption of UVB but not UVA light shows resistance to photobleaching.

FIG. 12A-L shows that the two tryptophan residues W77 and W328 in LITE-1 are required for LITE-1 function both in vivo and in vitro. (A-B) Mutating W77 and W328 but not the other four W residues disrupts the sensitivity of LITE-1 to both UVA and UVB light in vivo shown by behavioral assays. Wild-type (WT) and transgenic worms were exposed to a 20 sec pulse of UVA light (A), or UVB light (B). (C-F) W77F and W328F mutations disrupt the sensitivity of LITE-1 to UVA light in vivo shown by calcium imaging. Shades along the traces in (C-E) represent SEM. (F) Bar graph. $n \geq 6$. *$p<0.00001$ (ANOVA with Bonferroni test). (G-J) W77F and W328F mutations disrupt the sensitivity of LITE-1 to UVB light in vivo shown by calcium imaging. Shades along the traces in (G-I) represent SEM. (J) Bar graph. $n \geq 10$. *$p<0.00001$ (ANOVA with Bonferroni test). (K-L) W77F and W328F mutations disrupt LITE-1's absorption of both UVA and UVB light in vitro.

FIG. 13A-B shows that the two tryptophan residues W77 and W328 in LITE-1 are required for its sensitivity to both UVA and UVB light in vivo. (A-B) LITE-1$^{W77F}$ and LITE-1$^{W328F}$ were expressed as a transgene in muscle cells under the myo-3 promoter. UVA ($350 \pm 20$ nm, 0.8 mW/mm2) (A) or UVB ($280 \pm 10$ nm, 0.03 mW/mm2) (B) light was directed to the worm.

FIG. 14 shows sequence alignment of *C. elegans* GR family proteins, and additional data related to GUR-3. (A) The two tryptophan residues W77 and W328 in LITE-1 are marked with an asterisk. (B) Mutating Y79 to W in GUR-3 does not promote its sensitivity to UVA light in vivo shown by paralysis assay. (C-E) Mutating Y79 to W in GUR-3 does not promote its sensitivity to UVA light in vivo shown by calcium imaging. (C) and (D) Imaging traces. (E) Bar graph. $n=20$. $p=0.779$ (t test). (F-G) Mutating Y79 to W in GUR-3 promote its sensitivity to UVB but not UVA light in vivo shown by locomotion assay.

FIG. 15A-F shows additional data related to GUR-3. (A) Mutating Y79 to W in GUR-3 does not promote its sensitivity to UVA light in vivo shown by paralysis assay. (B-D) Mutating Y79 to W in GUR-3 does not promote its sensitivity to UVA light in vivo shown by calcium imaging. (B) and (C) Imaging traces. (D) Bar graph. $n=20$. $p=0.779$ (t test). (E-F) Mutating Y79 to W in GUR-3 promote its sensitivity to UVB but not UVA light in vivo shown by locomotion assay.

FIG. 16 shows the sequence of *C. elegans* LITE-1 peptide (SEQ ID NO:1).

FIG. 17 shows the sequence of *C. elegans* GUR-3 peptide (SEQ ID NO:2).

DEFINITIONS

Figure 1A:
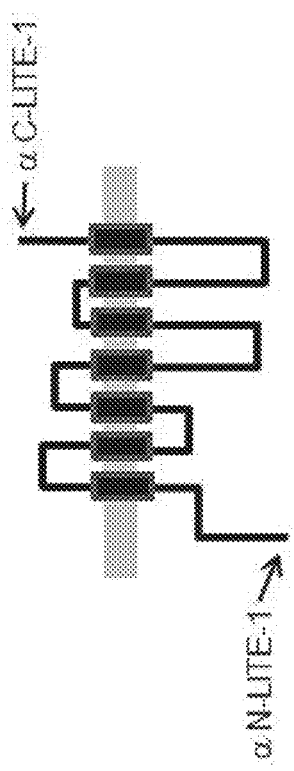
FIG. 1A-C shows that LITE-1 adopts an unusual membrane topology with its C-terminus facing extracellularly and N-terminus located intracellularly. (A) A schematic of LITE-1 membrane topology. (B) LITE-1 displays a distinct membrane topology with its C-terminus facing extracellularly and it N-terminus located in the cytoplasm. (C) BiFC images showing that the N-terminus of LITE-1 is located in the cytoplasm.

To facilitate an understanding of the present disclosure, a number of terms and phrases are defined below:

As used herein, the term "effective amount" refers to the amount of a therapeutic agent (e.g., a LITE-1 or GUR-3 polypeptide of the present disclosure) sufficient to effect beneficial or desired results. An effective amount can be administered in one or more administrations, applications or dosages and is not intended to be limited to a particular formulation or administration route.

As used herein, the term "co-administration" refers to the administration of at least two agent(s) (e.g., a peptide of the present disclosure) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

The term "topically acceptable", as used herein, means the ingredient is suitable for contact with human skin, including the scalp, without undue toxicity, incompatibility, irritation, instability, allergic response, and the like.

The term "sample" as used herein is used in its broadest sense. A sample may comprise a cell, tissue, or fluids, nucleic acids or polypeptides isolated from a cell, and the like.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "wildtype" when used in reference to a protein refers to proteins encoded by the genome of a cell, tissue, or organism, other than one manipulated to produce synthetic proteins.

The term "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; unnatural amino acids like p-aminophenylalanine, a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on). For an amino acid substitution, the following nomenclature is used: Original amino acid, position, substituted amino acid.

The relatedness between two amino acid sequences or between two nucleotide sequences is described by the parameter "identity". For purposes of the present disclosure, the degree of identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends in Genetics 16: 276-277), preferably version 3.0.0 or later. The optional parameters 11644.000-EP7 used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows: (Identical Residues×100)/(Length of Alignment−Total Number of Gaps in Alignment).

As used herein, the term "subject" refers to organisms to be treated by the methods of embodiments of the present disclosure. Such organisms preferably include, but are not limited to, mammals (e.g., murines, simians, equines, bovines, porcines, canines, felines, and the like), and most preferably includes humans. In the context of the disclosure, the term "subject" generally refers to an individual who will receive or who has received treatment (e.g., administration of a peptide of the present disclosure and optionally one or more other agents) for prevention of UV light induced damage or other condition requiring treatment.

DETAILED DESCRIPTION OF THE DISCLOSURE

Light sensation is critical for all phyla of life, ranging from bacteria to humans (Wang and Montell, Pflugers Arch 454, 821-847 2007; Yau and Hardie, Cell 139, 246-264 2009). Organisms have evolved various types of photoreceptor proteins (hereinafter referred to as photoreceptors) to detect light (Falciatore and Bowler, Curr Top Dev Biol 68, 317-350 2005; Wang and Montell, 2007, supra; Yau and Hardie, 2009, supra). These photoreceptors show different spectral properties with some sensing blue and others detecting green and red, covering a wide spectrum of light (Falciatore and Bowler, 2005, supra; Wang and Montell, 2007, supra; Yau and Hardie, 2009, supra). Photoreceptors are typically composed of two moieties: a host protein and a prosthetic chromophore (e.g. retinal), the latter of which is responsible for light absorption (Wang and Montell, 2007, supra; Yau and Hardie, 2009, supra). In addition to image-forming photoreceptor cells in the retina, a growing list of non-image-forming photosensitive cells/tissues has been identified in a wide range of animal species (Wang and Montell, 2007, supra; Yau and Hardie, 2009, supra). For example, a sub-set of ganglion and horizontal cells in the vertebrate retina are photosensitive (Yau and Hardie, 2009, supra). Photosensitive cells are also found in the skin (e.g. keratinocytes and melanocytes) of mammals, the pupil of most vertebrates, the pineal of non-mammalian vertebrates, the hypothalamus of birds, and the body surface of insects (Bellono et al., Proceedings of the National Academy of Sciences of the United States of America 110, 2383-2388 2013; Foster and Soni, Rev Reprod 3, 145-150 1998; Moore et al., Proceedings of the National Academy of Sciences of the United States of America 110, E3225-3234 2013; Xiang et al., Nature 468, 921-926 2010; Yau and Hardie, 2009, supra). However, in contrast to microbes and plants which express many types of photoreceptors, only two such groups of proteins have been identified in the animal kingdom: opsins and cryptochromes (Wang and Montell, 2007, supra; Yau and Hardie, 2009, supra). The question thus arises as to whether unknown types of photoreceptors exist in metazoans.

The nematode C. elegans detects and responds to a wide variety of sensory cues such as mechanical forces (e.g. touch and stretch), chemicals (e.g. odorants and tastants), and temperature, representing a popular genetic model organism for the study of sensory perception (de Bono and Maricq, Annu Rev Neurosci 28, 451-501 2005). Despite the lack of eyes, C. elegans also responds to light (Edwards et al., PLoS Biol 6, e198 2008; Ward et al., Nature Neurosci 11, 916-922 2008). Specifically, short wavelengths of light, particularly UV light, induce avoidance behavior (negative phototaxis) in C. elegans, which is mediated by a group of photosensory neurons, providing a protective mechanism for the worm to avoid lethal doses of UV in the sunlight (Liu et al., Nat Neurosci 13, 715-722 2010; Ward et al., 2008, supra). LITE-1, a member of the invertebrate seven-transmembrane (7-TM) gustatory receptor (GR) family, is required for UV light-induced avoidance behavior (Edwards et al., 2008, supra; Liu et al., 2010, supra). Ectopic expression of LITE-1 can confer photo-sensitivity to photo-insensitive cells (Edwards et al., 2008, supra; Liu et al., 2010, supra). Despite such indirect evidence providing LITE-1 as a candidate photoreceptor, other possibilities remain. For example, unlike long wavelengths of light, UV illumination produces reactive-oxygen-species (ROS) such as $H_2O_2$, which in turn can evoke an avoidance behavioral response similar to that induced by UV light (Bhatla and Horvitz, Neuron 85, 804-818 2015). Given that LITE-1 is a member of the gustatory receptor (GR) family, it has thus been stated that LITE-1 may function as a chemoreceptor (Yau and Hardie, 2009, supra). In this case, LITE-1 would sense light-produced chemicals but not light per se.

To address this conundrum, experiments conducted during the course of developing embodiments for the present disclosure purified LITE-1 protein from worm lysate and found that it directly absorbs UVA and UVB light. This property of LITE-1, together with its capacity in producing light-evoked functional outputs in vivo, indicates that LITE-1 is a photoreceptor. It was found that LITE-1 bears a number of unique features that distinguish it from other photoreceptors. These include an exceptionally high efficiency in photoabsorption, an ability to sense both UVA and UVB light, a strict dependence on conformation for photoabsorption, a strong resistance to bleaching by UV light, and a reversed membrane topology compared to opsins. These results identify LITE-1, a taste receptor homolog, as a unique photoreceptor with features not seen in any known photoreceptors. Thus, novel types of photoreceptors are present in the animal kingdom. Furthermore, such experiments identified two tryptophan residues in LITE-1 that are critical for photoabsorption. Remarkably, it was shown that introducing such a tryptophan residue into another GR family member promotes photosensitivity.

Accordingly, provided herein are compositions comprising LITE-1 and/or GUR-3 and cosmetic, pharmaceutical, and industrial uses thereof (e.g., to prevent UV-light damage to skin or eyes). Exemplary, non-limiting examples of compositions and, uses, and methods are described herein.

I. Compositions Comprising LITE-1 and/or GUR-3

As described herein, embodiments of the present disclosure provide compositions (e.g. cosmetic, pharmaceutical, or industrial compositions) comprising LITE-1 polypeptides.

A. Polypeptides and Peptides

The present disclosure is not limited to particular LITE-1 polypeptides or methods of obtaining LITE-1 polypeptides. In some embodiments, the LITE-1 polypeptide is a *C. elegans* LITE-1 polypeptide or fragments, mimetics, or variants thereof. For example, in some embodiments, the LITE-1 polypeptide is SEQ ID NO:1 or sequences at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:1. In some embodiments, the GUR-3 polypeptide is wild type *C. elegans* GUR-3 (e.g., SEQ ID NO:2 or sequences at least 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:2). In some embodiments, the GUR-3 polypeptide comprises one or more mutations (e.g., Y79W). In some embodiments, variants and fragments of LITE-1 or GUR-3 retain at least one activity of GUR-3 (e.g., ability to absorb UV-A and/or UB-B light).

In some embodiments, the present disclosure provides variants of LITE-1 or GUR-3 (e.g., mutation of one or more amino acids). In some embodiments, the mutation is not at position 77 or 328. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, and asparagine-glutamine.

Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic hydroxyl; (4) aromatic (phenylalanine, tyrosine, tryptophan); (5) amide (asparagine, glutamine); and (6) sulfur containing (cysteine and methionine) (e.g., Stryer ed., Biochemistry, pg. 17-21, 2nd ed., WH Freeman and Co., 1981).

In some embodiments, a variant includes "nonconservative" changes (e.g., replacement of a glycine with a tryptophan). Guidance in determining which amino acid residues can be substituted, inserted, or deleted without abolishing biological activity can be found using computer programs.

Percent sequence identity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

In some embodiments, 1, 2, 3, or 4 amino acids from the peptides described herein may be deleted. In some embodiments, 1, 2, 3, or 4 amino acids may be inserted into the peptides or added to either the C or N terminal end. In some embodiments, 1, 2, 3, or 4 amino acids within the peptides may be replaced with other amino acids (see above).

In some embodiments, a naturally occurring amino acid is replaced with, for example, a non-naturally occurring amino acid such as, for example, norleucine, ornithine, norvaline, homoserine, and other amino acid residue analogues such as those described in Ellman et al., Meth. Enzym., 1991, 202, 301-336. To generate such non-naturally occurring amino acid residues, the procedures of Noren et al., Science, 1989, 244, 182 and Ellman et al., supra, can be used. Other suitable methods are described in White et al., Methods, 2013, 60, 70-74; Gentilucci et al., Curr Pharm Des 2010, 16, 3195-3203; Hodgson & Sanderson, Chem Soc Rev 2004, 33, 422-430 and Krebs et al., Chemistry 2004, 10:544-553.

The LITE-1 polypeptides and peptides described herein can further be modified. Example of modifications include, but are not limited to, replace labile amino acids with ones that increase stability and improve activity, replace one or more L-amino acids with D-amino acids, reduce the size of the peptide (e.g., functional fragments of LITE-1), cyclize the peptide, internal hydrocarbon "stapling", that stabilizes peptide conformations, PEGylation of peptides or polypeptides, and C-terminal amidation or N-terminal acetylation as described in, for example, Brinckerhoff et al. (Int'l J. Cancer, 1999, 83, 326-334), or N-pyroglutamylation as described in, for example, Green et al. (J. Endocrinol., 2004, 180, 379-388), conjugation of various fatty acids ranging from 4-18 chain length as described in, for example, DasGupta et al. (Biol. Pharma. Bull., 2002, 25, 29-36), and.

In some embodiments, peptidomimetics of the peptides described herein are provided. Development of a small molecule peptidomimetic generally involves identification of the smallest functional peptide unit capable of inhibiting the targeted interaction. A growing body of literature demonstrates that high-affinity ligands can be selected from peptide libraries displayed on bacteriophage (Sulochana et al., Curr. Pharm. Des., 2007, 13, 2074-86; Cwirla et al., Proc. Natl. Acad. Sci. USA, 1990, 87, 6378-82; Scott et al., Science, 1990, 249, 386-90; and Devlin et al., Science, 1990, 249, 404-6), and many applications have been directed toward antagonizing the function of a protein ligand (Dower, Curr. Opin. Chem. Biol., 1998, 2, 328-34; and Sidhu et al., Methods Enzymol., 2000, 328, 333-63). Because the libraries can be very large (1011 or more individual members), no initial assumptions are required concerning how to bias the library, nor the selective enrichment of rare binding phage through biological amplification and rescreening. Those sequences that bind can be identified easily by sequencing their encoding DNA.

In some embodiments, peptide ligands such identified further serve as starting points for a combinatorial chemistry approach or a medicinal chemistry-based peptidomimetic approach for the development of new directed therapeutic agents. In addition, the determination of the structural basis for the high-binding affinity of these peptides for their substrate contributes to the rational design of a therapeutic agent.

LITE-1 and GUR-3 polypeptides and peptide fragments described herein are obtained or generated using any suitable method. In some embodiments, LITE-1 polypeptides are purified from *C. elegans* (See e.g., Example IX below). In some embodiments, LITE-1 or GUR-3 proteins of the present disclosure are isolated and purified from their natural sources by methods such as, preparing a soluble extract and enriching the extract using chromatographic methods on different solid support matrices. In some embodiments, a soluble extract of *C. elegans* is prepared in a buffer containing various protease inhibitors, followed by sequential chromatography of the extract through chromatograph columns (e.g., Sepharose matrix, cation-ion exchange matrix, gel filtration matrix, or reverse-phase matrix) or using the affinity purification method described herein. The fractions collected from such chromatography columns may be selected for the presence of LITE-1 or GUR-3 (e.g., by activity or size assay).

In some embodiments, nucleic acids encoding LITE-1 or GUR-3 polypeptides described herein are recombinantly produced (e.g. in mammalian, insect, fungi, or bacterial cells). Recombinant cDNA molecules encoding an LITE-1 or GUR-3 polypeptide is incorporated into an expression vector, this expression vector is introduced into an appropriate host cell, the host cell is cultured, and the expressed protein is isolated.

Expression vectors are DNA sequences that are required for the transcription of cloned copies of genes and translation of their mRNAs in an appropriate host. These vectors can express either procaryotic or eucaryotic genes in a variety of cells such as bacteria, yeast, mammalian, plant and insect cells. Proteins may also be expressed in a number of virus systems.

Suitably constructed expression vectors contain an origin of replication for autonomous replication in host cells, or are capable of integrating into the host cell chromosomes. Such vectors will also contain selective markers, a limited number of useful restriction enzyme sites, a high copy number, and strong promoters. Promoters are DNA sequences that direct RNA polymerase to bind to DNA and initiate RNA synthesis; strong promoters cause such initiation at high frequency. The preferred expression vectors of the present disclosure are operatively linked to a recombinant cDNA molecule of the present disclosure, i.e., the vectors are capable directing both replication of the attached recombinant cDNA molecule and expression of the protein encoded by the recombinant cDNA molecule. Expression vectors may include, but are not limited to cloning vectors, modified cloning vectors and specifically designed plasmids or viruses.

Suitable host cells for expression of the proteins of the present disclosure include bacteria, yeast, mammalian, plant and insect cells. With each type of cell and species therein certain expression vectors are appropriate as will be disclosed below.

Procaryotes may be used for expression of the proteins of the present disclosure. Suitable bacteria host cells include the various strains of *E. coli, Bacillus subtilis*, and various species of *Pseudomonas*. In these systems, plasmid vectors which contain replication sites and control sequences derived from species compatible with the host are used. Suitable vectors for *E. coli* are derivatives of pBR322, a plasmid derived from an *E. coli* species by Bolivar et al., Gene, 2:95 (1977). Common procaryotic control sequences, which are defined herein to include promoters for transcription, initiation, optionally with an operator, along with ribosome binding site sequences, include the beta-lactamase and lactose promoter systems (Chang et al., Nature, 198: 1056 (1977)), the tryptophan promoter system (Goeddel et al., Nucleic Acids Res., 8:4057 (1980)) and the lambda-derived-PL promoter and N-gene ribosome binding site (Shimatake et al., Nature, 292:128 (1981)). However, any available promoter system compatible with procaryotes can be used. Preferred procaryote expression systems include *E. coli* and their expression vectors.

Eucaryotes may be used for expression of the proteins of the present disclosure. Eucaryotes are usually represented by the yeast and mammalian cells. Suitable yeast host cells include *Saccharomyces cerevisiae* and *Pichia pastoris*. Suitable mammalian host cells include COS and CHO (chinese hamster ovary) cells.

Expression vectors for the eucaryotes are comprised of promoters derived from appropriate eucaryotic genes. Suitable promoters for yeast cell expression vectors include promoters for synthesis of glycolytic enzymes, including those for 3-phosphoglycerate kinase gene in *Saccharomyces cerevisiae* (Hitzman et al., J. Biol. Chem., 255:2073 (1980)) and those for the metabolism of methanol as the alcohol oxidase gene in *Pichia pastoris* (Stroman et al., U.S. Pat. Nos. 4,808,537 and 4,855,231). Other suitable promoters include those from the enolase gene (Holland, M. J. et al., J. Biol. Chem., 256:1385 (1981)) or the Leu2 gene obtained from YEp13 (Broach, J. et al., Gene, 8:121 (1978)).

Preferred yeast expression systems include *Pichia pastoris* and their expression vectors.

Suitable promoters for mammalian cell expression vectors include the early and late promoters from SV40 (Fiers, et al., Nature, 273:113 (1978)) or other viral promoters such as those derived from polyoma, adenovirus II, bovine papilloma virus or avian sarcoma viruses. Suitable viral and mammalian enhancers may also be incorporated into these expression vectors.

Suitable promoters for plant cell expression vectors include the nopaline synthesis promoter described by Depicker, A. et al., Mol. Appl. Gen., 1:561 (1978).

Suitable promoters for insect cell expression vectors include modified versions of the system described by Smith et al., U.S. Pat. No. 4,745,051. The expression vector comprises a baculovirus polyhedrin promoter under whose control a cDNA molecule encoding a protein can be placed.

Host cells are transformed by introduction of expression vectors of the present disclosure into them. Transformation is done using standard techniques appropriate for each type of cell. The calcium treatment employing calcium chloride described in Cohen, S. N., Proc. Natl. Acad. Sci. USA, 69:2110 (1972), or the RbC1 method described in Maniatis et al., *Molecular Cloning: A Laboratory Manual*, p. 254, Cold Spring Harbor Press (1982) is used for procaryotes or other cells which contain substantial cell wall barriers. The transformation of yeast is carried out as described in Van Solingen, P. et al., J. Bacter., 130:946 (1977) and Hsiao, C. L. et al., Proc. Natl. Acad. Sci. USA, 76:3829 (1979). Mammalian cells without much cell wall are transformed using the calcium phosphate procedure of Graham and van der Eb, Virology, 52:546 (1978). Plant cells are transformed by infection with *Agrobacterium tumefaciens* as described in Shaw, C. et al, Gene, 23:315 (1983). Preferred methods of transforming *E. coli* and *Pichia pastoris* with expression vectors include electroporation.

Transformed host cells are cultured under conditions, such as type of media, temperature, oxygen content, fluid motion, etc., well known in the biological arts and purified as described herein.

In some embodiments, peptides are synthesized de novo. A variety of peptide synthesis methods may be utilized. Examples include, but are not limited to, solid-phase peptide synthesis (SPPS), (R. B. Merrifield (1963). "Solid Phase Peptide Synthesis. I. The Synthesis of a Tetrapeptide". J. Am. Chem. Soc. 85 (14): 2149-2154; Mitchell, A. R. K., S. B. H.; Engelhard, M.; Merrifield, R. B. (1978). "A new synthetic route to tert-butyloxycarbonylaminoacyl-4-(oxymethyl)phenylacetamidomethyl-resin, an improved support for solid-phase peptide synthesis". J. Org. Chem. 43 (13): 2845-2852). Recent developments in synthesis methods are further described in Hojo, Curr Opin Struct Biol 2014, 26C, 16-23; Ramakers et al., Chem Soc Rev 2014, 43, 2743-2756 and Chandrudu et al., Molecules 2013, 18, 4373-4388.

In SPPS, Small solid beads, insoluble yet porous, are treated with functional units ('linkers') on which peptide chains can be built. The peptide will remain covalently attached to the bead until cleaved from it by a reagent such as anhydrous hydrogen fluoride or trifluoroacetic acid. The peptide is thus 'immobilized' on the solid-phase and can be retained during a filtration process, whereas liquid-phase reagents and by-products of synthesis are flushed away.

The general principle of SPPS is one of repeated cycles of coupling-wash-deprotection-wash. The free N-terminal amine of a solid-phase attached peptide is coupled (see below) to a single N-protected amino acid unit. This unit is then deprotected, revealing a new N-terminal amine to which a further amino acid may be attached. The superiority of this technique partially lies in the ability to perform wash cycles after each reaction, removing excess reagent with all of the growing peptide of interest remaining covalently attached to the insoluble resin.

There are two majorly used forms of SPPS—Fmoc and Boc. Unlike ribosome protein synthesis, solid-phase peptide synthesis proceeds in a C-terminal to N-terminal fashion. The N-termini of amino acid monomers is protected by either of these two groups and added onto a deprotected amino acid chain.

B. Formulations

Embodiments of the present disclosure provide cosmetic, pharmaceutical, and industrial compositions and formulations.

In some embodiments, topical pharmaceutical and cosmetic compositions include, but are not limited to, ointments, creams, lotions, oils, gels, lips ointments, sunscreen, sticks, sprays, pastes, mousses, and aerosols.

Topical compositions, for example, cosmetic or pharmaceutical formulations, comprising LITE-1 and/or GUR-3 polypeptides described herein may further comprise other topically acceptable ingredients known to those skilled in the art, such as, for example, at least one ingredient selected from the group consisting of preservatives, emollients, emulsifying agents, surfactants, moisturizers, gelling agents, thickening agents, conditioning agents, film-forming agents, stabilizing agents, anti-oxidants, texturizing agents, gloss agents, mattifying agents, solubilizers, pigments, dyes, and fragrances.

In one embodiment, the cosmetic composition of the disclosure is in the form of an anti-wrinkle or anti-aging cream, in particular intended to be applied on skin termed "aged" (e.g., skin from an individual having a chronological age of 40 or more years), a composition for sensitive and/or irritated skin, or a product for making up the skin of the face, body or lips such as a foundation or a lipstick. In one advantageous embodiment, the cosmetic composition of the disclosure is a composition protecting skin against UV damages, notably a sunscreen composition.

The LITE-1 or GUR-3 polypeptides described herein may be used as the sole active component in a cosmetic or pharmaceutical formulation, or in combination with one or more active components. Advantageous topical cosmetic or pharmaceutical compositions may comprise a LITE-1 and/or GUR-3 polypeptide and one or more proteases selected from the group papain, ficin, bromelain, and actinidin. In one example embodiment, the proteases are stabilized proteases, and more preferably, one or more proteases may be stabilized proteases formed by crosslinking such as those described in US 2011-0177052 (Chavan), incorporated herein by reference. Further advantageous topical cosmetic or pharmaceutical compositions comprise a LITE-1 and/or GUR-3 polypeptide and one or more additional skin care ingredients capable of stimulating, improving or otherwise regulating proteasome activity in the skin, such as, by way of example, those described in US 2009-0130139 (Mekideche), U.S. Pat. No. 7,220,417 (Nizard et al), and U.S. Pat. No. 7,919,468 (Reboud-Ravaux, et al), all of which are incorporated herein by reference.

Additional topical cosmetic or pharmaceutical compositions may comprise one or more additional marine-derived topical skin care ingredients having similar, additional, and/or complementary beneficial skin effects. By way of example, suitable additional marine-derived topical skin care ingredients for use in such topical compositions may include those described in US 2010-0047219 (Ceccoli et al), US 2010-0316720 (Statz et al), US 2009-0142370 (Shih et al), U.S. Pat. No. 7,128,914 (Leclerc et al), U.S. Pat. No. 7,220,517 (Nizard et al), all of which are incorporated herein by reference, and *Chondrus crispus* extract.

The CTFA Cosmetic Ingredient Handbook, Second Edition (1992) describes various cosmetic and pharmaceutical active and inactive ingredients that are suitable for topical use and may be used in combination with LITE-1 and/or GUR-3. Non-limiting examples of these classes of ingredients include the following compounds: abrasives, absorbants, compounds with an aesthetic aim such as fragrances, pigments, dyes, essential oils, astringents, etc (for example: clove oil, menthol oil, camphor oil, eucalyptus oil, eugenol, menthyl lactate, witch hazel distillate), anti-acne agents (for example, salicylic acid or benzoyl peroxide), anti-flocculants, anti-foaming agents, antimicrobial agents (for example: iodopropyl butylcarbamate), anti-oxidants (for example, ascorbic acid and its derivatives or tea extracts), anti-wrinkle actives (for example, retinoids or beta-hydroxy acids), binders, biological additives, buffers, swelling agents, chelating agents, additives, biocidal agents, denaturing agents, thickening agents, and vitamins, and their derivatives or equivalents, film-forming materials, polymers, opacifying agents, pH adjusters, reducing agents, de-pigmenting or brightening agents (for example: hydroquinone, kojic acid, ascorbic acid, mulberry extract, magnesium ascorbyl phosphate, ascorbyl glucosamine), conditioning agents (for example: humectants), anti-inflammatory agents (for example, corticosteroids), and sunscreens.

In some embodiments, composition comprise one or more physiologically suitable solvents, classically used by a person skilled in the art, such as water, glycerol, ethanol, propanediol, butylene glycol, dipropylene glycol, ethoxylated or propoxylated diglycols, cyclic polyols, or any mixture of these solvents.

According to yet another advantageous embodiment of the disclosure, the LITE-1 polypeptide according to the disclosure is solubilized in a cosmetic or pharmaceutical vector such as liposomes, or adsorbed on powdery organic polymers, mineral supports such as talcs and bentonites, and more generally solubilized in, or fixed on, any physiologically suitable vector.

In some embodiments, LITE-1 and/or GUR-3 polypeptides are present in the composition at a concentration of between around 0.0005 and 500 ppm, and optionally at a concentration of between 0.01 and 5 ppm.

In some embodiments, the composition according to the disclosure also contains at least one additional active ingredient. It is possible to cite, in a non-limiting manner, the following classes of ingredients:

sunscreens, ultraviolet and infrared screens anti-free radical agents,

DHEA (dehydroepiandrosterone), —vitamin A and notably retinoic acid, retinol, retinol proprionate, retinol palmitate, vitamin B3 and notably niacinamide, niconitate of tocopherol, vitamin B5, vitamin B6, vitamin B12, panthenol, vitamin C, and notably ascorbic acid, ascorbyl glucoside, ascorbyl tetrapalmitate, magnesium and sodium ascorbyl phosphate, vitamins E, F, H, K, PP, and coenzyme Q10, metalloproteinase inhibitor, activator of TIMP, aminoacids and notably arginine, ornithine, hydroxyproline, hydroxyproline dipalmitate, palmitoylglycine, hydroxylysine, methionine and its derivatives, N-acylated aminoacids, natural or synthetic peptides, including, di-, tri-, tetra-, penta- and hexapeptides and their lipophilic derivatives, isomers and complex with other molecules such as metallic ion (i.e. copper, zinc, manganese, magnesium, and others), peptides sold under commercial names MATRIXYL®, ARGIRELINE®, COLLAXYL™, PEPTIDE VINCI 02™, CHRONOGEN™, LAMINIXYL IS™, PEPTIDE Q10™, peptidic plant extracts obtained by hydrolysis or any other methods such as soy extract, einkorn extract, *Vitis vinifera* extract, rapeseed extract, flaxseed extract rice extract, corn extract, or pea extract, carob extract, bean extract, fava extract, yeast extract, anemia sauna extract, dehydroacetic acid (DHA), natural or synthetic phytosterols, alpha- and beta-hydroxyacids, silanols, sugar amines, glucosamine, D-glucosamine, N-acetyl-glucosamine, N-acetyl-D-glucosamine, mannosamine, N-acetyl mannosamine, galactosamine, N-acetyl galactosamine, polyphenols, isoflavones, flavonoids, such as grape extract, pine extract, olive extract, lipids such as ceramides or phospholipids, animal oils such as squalenes or squalanes, vegetal oils, such as almond oil, coconut oil, castor oil, jojoba oil, olive oil, rapeseed oil, peanut oil, sunflower oil, wheat germ oil, corn germ oil, soybean oil, cotton oil, alfalfa oil, poppy oil, pumpkin seed oil, evening primrose oil, millet oil, barley oil, rye oil, safflower oil, passion oil, hazelnut oil, palm oil, apricot kernel oil, avocado oil, calendula oil, ethoxylated vegetable oils, or shea butter, Said compounds above can be natural, such as plant peptide hydrolysates, or of synthetic origin, such as peptide compounds.

In addition, additives such as solvents, diluents, dyes, sunscreens, self-tanning agents, pigments, fillers, preservatives, odor absorbents, thickening agents, emulsifiers, moistening agents, emollients, fragrances, antioxidants, film-forming agents, chelating agents, sequestering agents and conditioners can be added to the composition.

The present disclosure further provides industrial compositions comprising the LITE-1 polypeptides described herein. In some embodiments, such compositions find use in protecting against UVA and/or UVB light. In some embodiments, LITE-1 polypeptides are embedded in films or coatings (e.g., for use on lenses such as sunglasses or eyeglasses, windows, car windows, etc.).

II. Methods of Use

In some embodiments, the composition described herein find use in protection against UVA and/or UVB light. In some embodiments, topical formulations find use in protecting skin agains damaging UV light. For example, in some embodiments, a subject applies such formulations to skin on a regular (e.g., daily or multiple times a day) basis to prevent skin damage. In some embodiments, a subject applies compositions comprising LITE-1 to skin prior to and/or during sun exposure.

In some embodiments, LITE-1 and/or GUR-3 polypeptides or films or coatings comprising LITE-1 and/or GUR-3 polypeptides are incorporated into lenses (e.g., eyeglass, sunglass, or contact lenses) to protect eyes again sun exposure. In some embodiments, LITE-1 and/or GUR-3 polypeptides films or coatings comprising LITE-1 and/or GUR-3 polypeptides are incorporated into windows, car windshields, or other structural elements in order to protect agains sun exposure.

EXPERIMENTAL

The following examples are provided in order to demonstrate and further illustrate certain preferred embodiments and aspects of the present disclosure and are not to be construed as limiting the scope thereof.

Example I

This example demonstrates that LITE-1 adopts a membrane topology opposite to conventional 7-TM receptors.

Figure 1B:
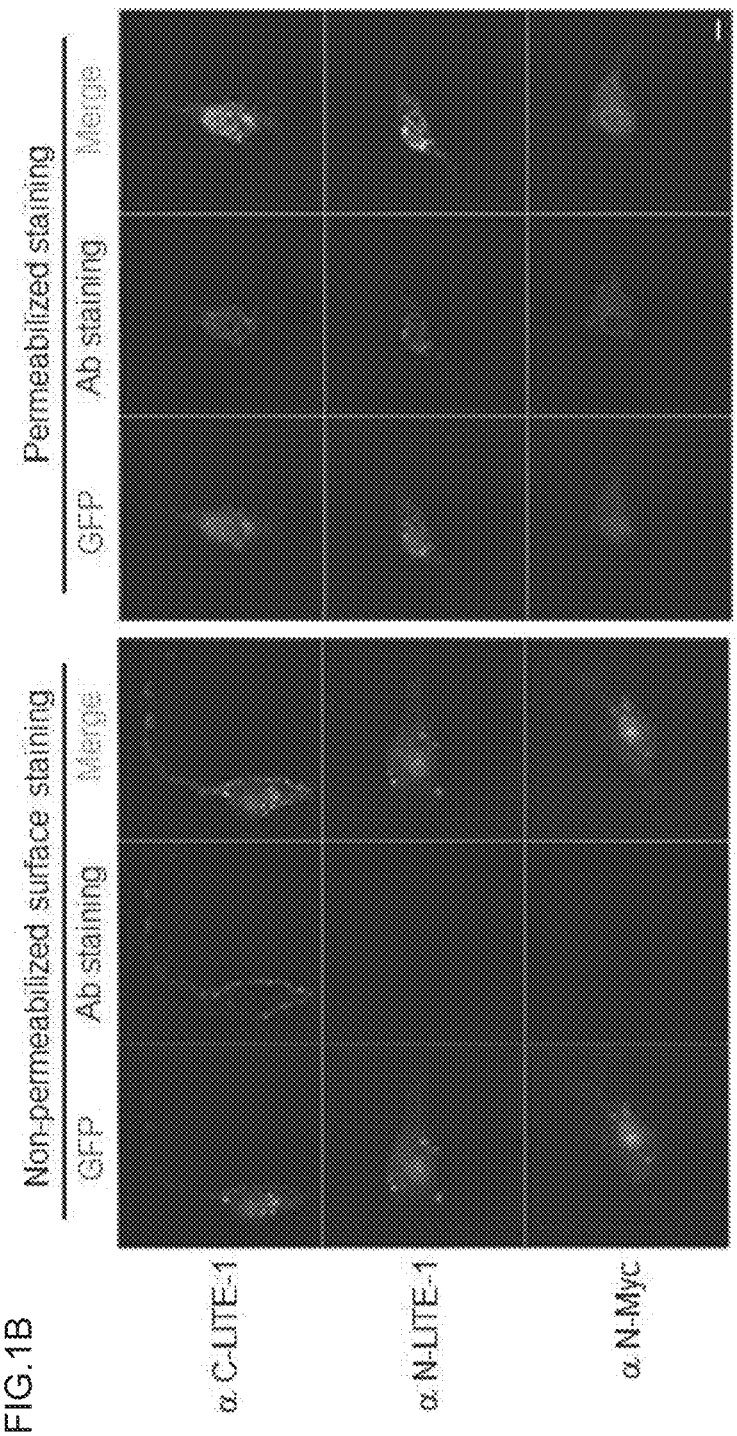
Figure 2:
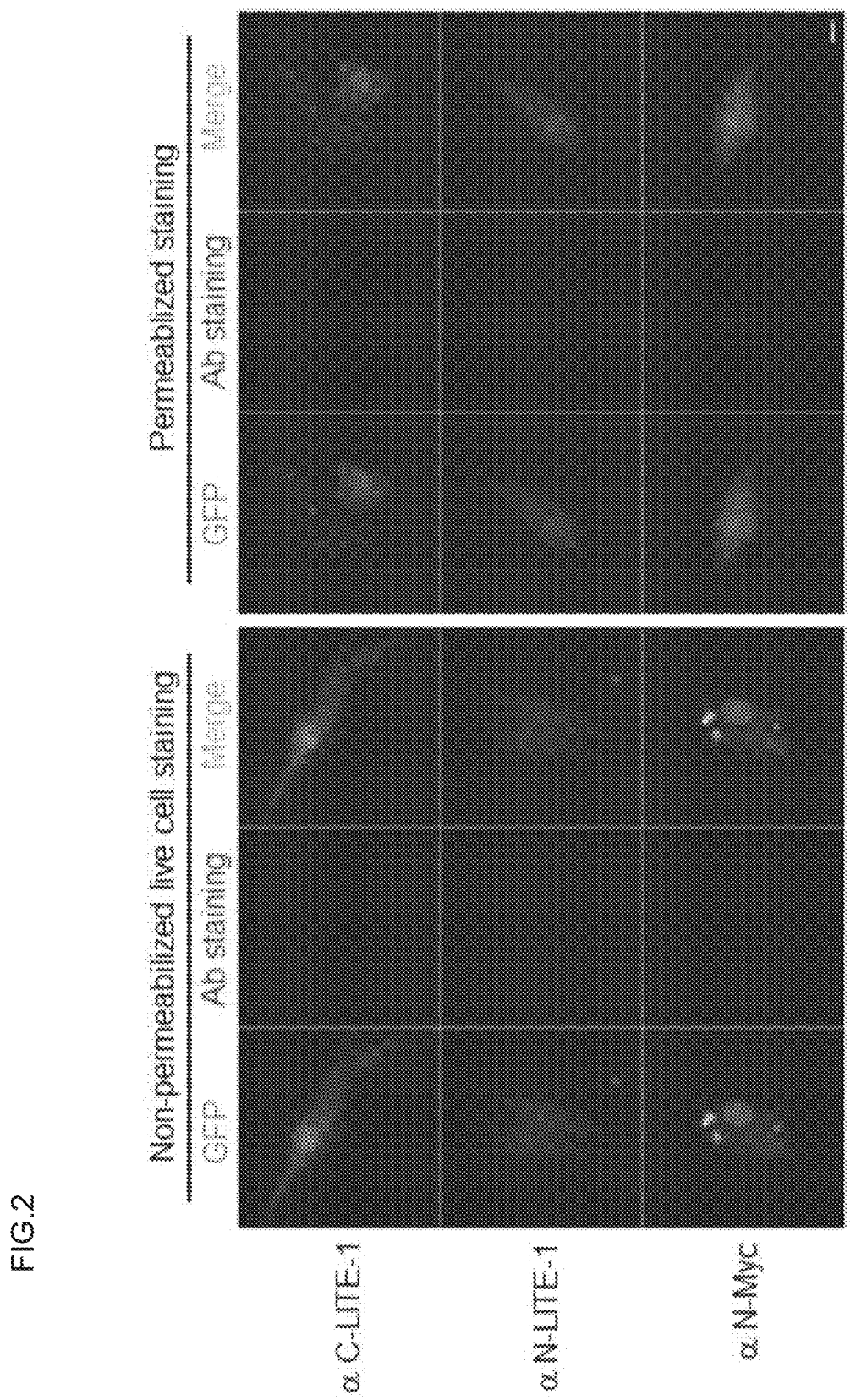
FIG. 2 shows control images for FIG. 1B.

As a first step, it was considered whether LITE-1 is related to any known photoreceptors. LITE-1 is predicted to contain 7-TM domains (FIG. 1A). The only known 7-TM photoreceptors in metazoans are opsins, but LITE-1 has no significant homology with opsins at the sequence level (Edwards et al., 2008, supra; Liu et al., 2010, supra). As both insect OR (olfactory receptors) and GR (gustatory receptors) members were shown to possess a membrane topology opposite to conventional 7-TM receptors (Benton et al., PLoS Biol 4, e20 2006; Zhang et al., PloS one 6, e24111 2011), it was thus questioned whether LITE-1 and opsins are even related at the membrane topology level. To probe the membrane topology of LITE-1, antibodies were raised against the N- and C-termini of LITE-1 (FIG. 1A). Immunostaining with these antibodies did not reveal consistent LITE-1 expression in worm tissues, indicating that LITE-1 is expressed at a very low level in vivo. Transgenic animals were therefore generated expressing LITE-1 in muscle cells using a muscle-specific promoter, as LITE-1 can be functionally expressed in these cells at a higher level, though it remains possible that recombinant LITE-1 may not fully preserve all the functional properties of native proteins (Edwards et al., 2008, supra; Liu et al., 2010, supra). It was found that the LITE-1 antibodies can detect LITE proteins in primary cultured muscle cells (FIG. 1B). Surprisingly, the C-terminal end of LITE-1 appears to be extracellular, as antibodies against LITE-1's C-terminus can detect LITE-1 when applied extracellularly under non-permeabilizing conditions (FIG. 1B). This staining is specific for LITE-1 since no signal was observed in control muscle cells (FIG. 2). By contrast, the same protocol failed to detect LITE-1 with antibodies against its N-terminal end, though the protein was clearly expressed in these cells as shown under permeabilizing conditions (FIG. 1B). To provide additional evidence, a Myc tag was fused to the N-terminal end of LITE-1 and obtained the same result (FIG. 1B). This indicates that the N-terminal end of LITE-1 is intracellular.

Figure 1C:
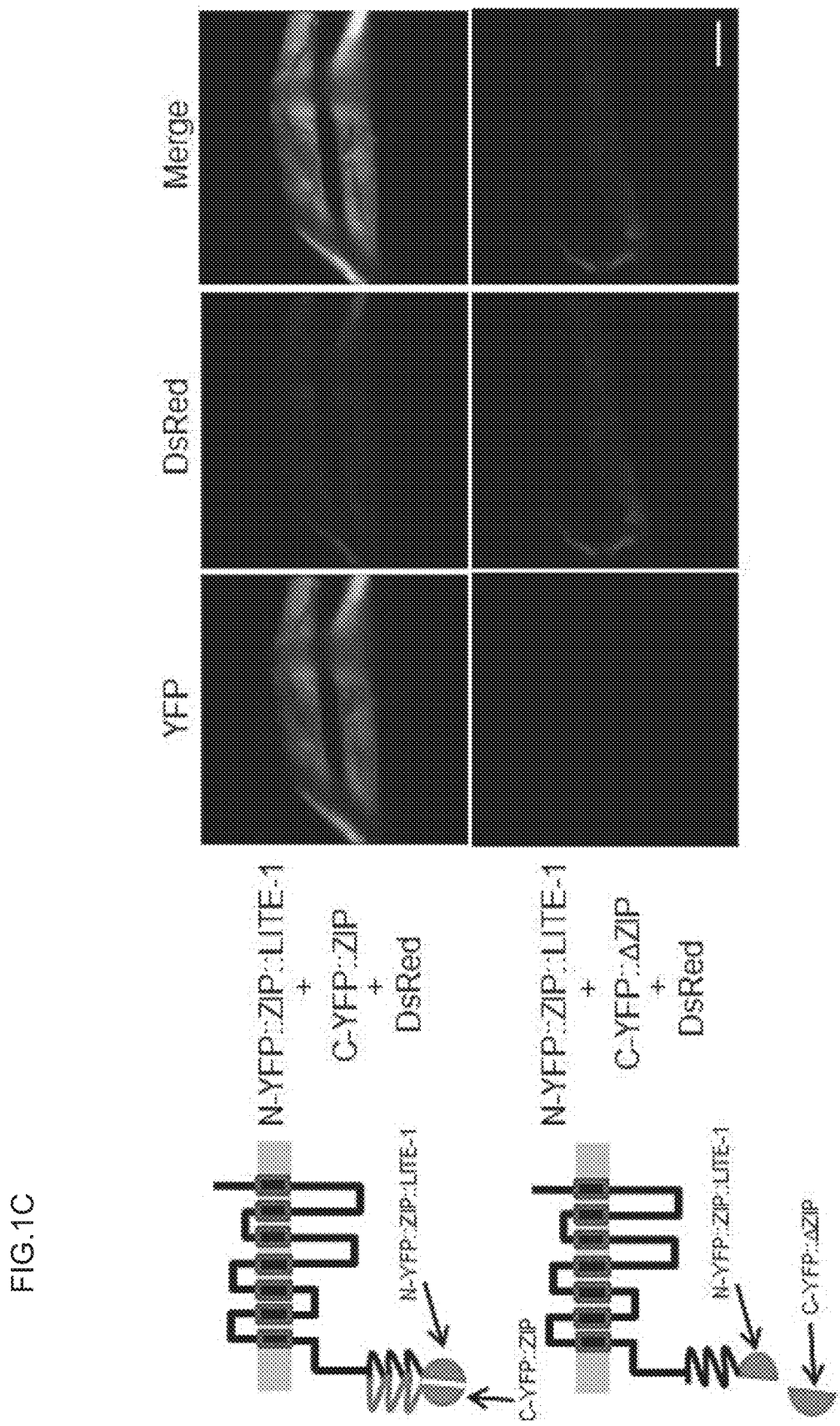

To collect further evidence, the BiFC (Bimolecular Fluorescence Complementation) approach (Hu et al., Mol Cell 9, 789-798 2002) was employed. In this approach, the N- and C-terminal fragment of YFP is fused to a leucine zipper domain to generate N-YFP::ZIP and C-YFP::ZIP, respectively (FIG. 1C). The zipper domains then bring the two YFP fragments together to reconstitute a fluorescent YFP protein (FIG. 1C). N-YFP::ZIP was attached to the N-terminus of LITE-1, and it was found that this N-YFP::ZIP::LITE-1 fusion complemented with C-YFP::ZIP to reconstitute YFP fluorescence in live muscle cells acutely dissected from the animal, but not with C-YFP::ΔZIP that lacked the zipper domain (FIG. 1C). This observation further demonstrates that the N-terminus of LITE-1 is located intracellularly. It was concluded that LITE-1 adopts a reversed membrane topology compared to opsins. Thus, LITE-1 does not seem to be closely related to any known photoreceptors at the sequence or structural levels.

Example II

This example demonstrates the purification of LITE-1 protein from worm lysate.

Examples were conducted asking the question—is LITE-1 a photoreceptor? A lack of clear similarity to known photoreceptors does not necessarily disqualify LITE-1 as a photoreceptor. To address this question, a simple, yet definitive approach is to examine whether purified LITE-1 protein can capture photons by spectrophotometry (Wang and Montell, 2007, supra; Yau and Hardie, 2009, supra). All known photoreceptors were verified by this approach (FIG. 3C). To this end, an expression system was searched for that would allow us to purify a sufficient amount of LITE-1 protein for spectrophotometric analysis. Muscle cells thus came to attention, as they constitute a major mass of worm tissues and have been successfully utilized as a heterologous system to functionally express receptors and channels (Salom et al., FASEB J 26, 492-502 2012; Wang et al., Neuron 75, 838-850 2012). Importantly, it has been shown that LITE-1 can be functionally expressed in muscles, as its expression can confer photo-sensitivity to these otherwise photo-insensitive cells (Edwards et al., 2008, supra; Liu et al., 2010, supra), though it remains unclear whether such photosensitivity results from light or light-produced chemicals. Indeed, as previously reported (Edwards et al., 2008, supra; Liu et al., 2010, supra), UV light can induce the contraction of body-wall muscles ectopically expressing LITE-1, leading to body paralysis (FIG. 4A, FIG. 5). To provide more direct and quantitative evidence, the response of muscle cells to UV light was recorded by calcium imaging using the genetically-encoded calcium sensor RCaMP. It was found that UV illumination induced robust calcium transients in muscle cells ectopically expressing LITE-1, but not in control muscle cells (FIG. 4B-D). These experiments show that LITE-1 was functionally expressed in muscle cells. They also show that LITE-1 can indeed confer photo-sensitivity to photo-insensitive cells, demonstrating that it can be potentially used as an optogenetic tool.

Since the LITE-1 antibodies are not suitable for affinity-purification, a number of monoclonal antibodies against small affinity tags such as Myc, FLAG, and 1D4 were tested, and it was found that 1D4 antibody worked most efficiently. Using this antibody, it was able to affinity-purify LITE-1, a membrane protein, to homogeneity, as determined by SDS-PAGE followed by coomassie staining (FIG. 4E), and by Western blot (FIG. 4F). This result was also verified by silver staining.

Example III

This example demonstrates that purified LITE-1 protein absorbs photons

By subjecting purified LITE-1 protein to spectrophotometric analysis, it was found that it exhibited strong absorption of UV light, with two absorbance peaks at 280 nm and 320 nm (FIG. 4G). Thus, LITE-1 can capture both UVB and UVA light (WHO definition of UVB: 280-315 nm; UVA: 315-400 nm). As a comparison, at the same concentration (0.4 µM), BSA showed no such absorption (FIG. 4G). In addition, bacterial rhodopsin (bRho), which is a commercial product obtained from Sigma Co., exhibited minimal absorption at its signature peak 568 nm (FIG. 4H). Only at 10×concentration (4 µM) was it possible to detect modest light absorption in bacterial rhodopsin (bRho), which was still much weaker than that found in LITE-1 (FIG. 4H). It should be noted that though bRho exhibited weaker photoabsorption compared to LITE-1, its extinction coefficient (62,000 in FIG. 4H vs. 63,000 in FIG. 4I), as well as its spectral properties, were both in line with those reported in literature (FIG. 4H-I), indicating that the quality of bRho samples was reliable. The extinction coefficient of both absorbance peaks of LITE-1 is >$10^6$ $M_{-1}cm^{-1}$, which is 10-100 times that of all known photoreceptors (FIG. 4I). Thus, LITE-1 has a high efficiency in capturing photons.

To make a more direct comparison, purified bovine rhodopsin (Rho) was ectopically expressed in worm muscles (Salom et al., 2012, supra), and was done side-by-side with LITE-1 under the same conditions (FIG. 6A-B). Compared to LITE-1, purified bovine rhodopsin (Rho) also showed much weaker photoabsorption at its signature peak (FIG. 6C-D), providing additional evidence demonstrating that LITE-1 is highly efficient in capturing photons. The relatively weak photoabsorption by bovine rhodopsin (Rho) was not because the purified Rho samples were of low quality, as the extinction coefficient of the purified Rho was in fact very similar to that reported in literature (FIG. 6D vs. FIG. 4I). In addition, the signature absorbance peak of the purified Rho was 500 nm, which was identical to that published in literature (FIG. 6D vs. FIG. 21). This set of control experiments also validated the experimental system, including protein expression, purification, concentration determination, and spectral analysis.

In another control experiment, purified mammalian adenosine $A_{2A}$ receptor ($A_{2A}R$) was ectopically expressed in worm muscles (Salom et al., 2012, supra) (FIG. 6A-B). Like LITE-1 and opsins, $A_{2A}R$ is also a 7-TM receptor but not expected to be photosensitive. Indeed, it was found that as predicted, this receptor did not absorb light when purified and tested side-by-side with LITE-1 and bovine Rho (Figure GC). Thus, multiple control experiments support that LITE-1 absorbs photons and does so at a high efficiency. This property of LITE-1, together with its capacity in producing various light-induced functional outputs [e.g. light-induced muscle contraction and calcium transients, and avoidance behavior (FIG. 4A-D, FIG. 5), indicates that LITE-1 is a photoreceptor. LITE-1 is also the only photoreceptor that shows strong absorption of both UVA and UVB light.

Example IV

This example demonstrates that LITE-1 strictly depends on its conformation for photoabsorption.

Experiments next sought to characterize the photoabsorption of LITE-1. A photoreceptor is usually composed of two moieties: a host protein and a prosthetic chromophore (Falciatore and Bowler, Curr Top Dev Biol 68, 317-350 2005; Wang and Montell, 2007, supra; Yau and Hardie, 2009, supra). The spectral properties of a photoreceptor are certainly affected by the host protein. However, the absolute ability of a photoreceptor to absorb light does not rely on the host protein, as light absorption is mediated by the chromophore (e.g. retinal, flavin, bilin, and p-coumaric acid) (Falciatore and Bowler, 2005, supra; Marti et al., J Biol Chem 266, 18674-18683 1991; Radding and Wald, J Gen Physiol 39, 909-922 1956). Consequently, denaturing a photoreceptor usually shifts its absorbance peaks to different wavelengths but does not eliminating them, as they are mediated by the associated chromophore (Dutta et al., Biochemistry 49, 6329-6340 2010; Hagins, J Biol Chem 248, 3298-3304 1973; Hubbard, Nature 221, 432-435 1969; Maglova et al., Biochimica Et Biophysica Acta 975, 271-276 1989). This, surprisingly, does not appear to the case for LITE-1. Denaturing LITE-1 with urea completely abolished the light absorption by LITE-1, eliminating both the 280 and 320 nm peaks (FIG. 3A). As a comparison, the same urea treatment failed to abolish the light absorption by bacterial rhodopsin (bRho), but instead shifted its absorbance peak from 568 nm to 370 nm (FIG. 3B), the latter of which is the signature peak of free retinal, the chromophore of bRho (Sperling and Rafferty, 1969). A similar phenomenon was observed with the purified bovine rhodopsin (Rho) (FIG. 3E-F). It is notable that the 280 nm peak of denatured bRho remained unchanged (FIG. 3B), consistent with the notion that this peak was mediated by the intrinsic light absorption by tryptophan residues of the bRho protein. This peak was not that distinct in denatured LITE-1 in FIG. 3A since the concentration of LITE-1 used was 1/10 that of bRho. LITE-1 was also treated using other denaturing agents such as NaOH, and observed a similar phenomenon (FIG. 3C-D). These observations demonstrate that unlike typical photoreceptors, LITE-1 strictly depends on its conformation for photoabsorption.

Experiments also tested $H_2O_2$. Interestingly, $H_2O_2$ treatment completely abolished LITE-1's photoabsorption (FIG. 7A). As an oxidizing agent, $H_2O_2$ can damage the function of proteins, lipids and nucleic acids (Fridovich, Med Princ Pract 22, 131-137 2013). Oxidization of LITE-1 may affect the conformation of LITE-1, which is required for its absorption of light. Similarly, $H_2O_2$ treatment also destroyed the spectral fingerprint of bRho by shifting its absorbance peak from 568 nm to 370 nm (FIG. 7B). Thus, $H_2O_2$ appears to inhibit the photoabsorption of both LITE-1 and bRho in vitro.

Example V

This example demonstrates that genetic screens identify residues critical for LITE-1 function.

Figure 8E:
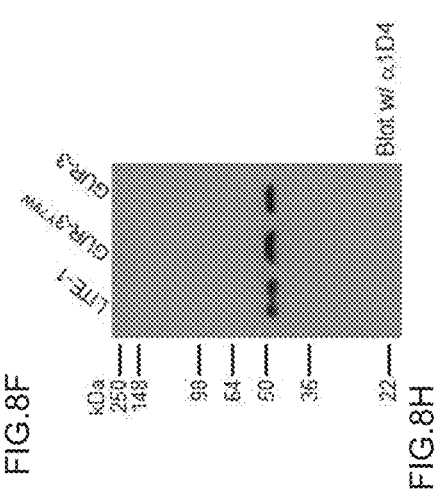
Figure 8F:

To obtain a better understanding of LITE-1 photoabsorption, experiments attempted to identify residues critical for LITE-1 function. In a genetic screen for mutant animals defective in UV light-induced avoidance behavior, several lite-1 mutant alleles (Liu et al., 2010, supra) were isolated. It was hypothesized that mutations in transmembrane domains are more likely to affect the photoabsorption of LITE-1 rather than its coupling to downstream signaling molecules. Two mutants, lite-1(xu8) and lite-1(xu10), thus came to attention, as the residues mutated (A332V and S226F, respectively) reside in putative transmembrane domains (FIG. 8I). The objective was to purify these mutant forms of LITE-1 protein and then characterize their photoabsorption in vitro. Experiments first tested their role in vivo, and it was found that as expected, A332V and S226F mutations disrupted LITE-1 function in vivo. Specifically, worms ectopically expressing LITE-1 harboring either mutation were no longer sensitive to UVA light in behavioral assays (FIGS. 9A and 10A). In addition, these two point mutations nearly abolished UVA light-evoked calcium transients in muscle cells ectopically expressing LITE-1 (FIG. 9B-E). Experiments successfully purified LITE-1$^{A332V}$ and LITE-1$^{S226F}$ proteins to homogeneity (FIG. 9F-G). LITE-A332V and LITE-1$^{S226F}$ displayed an absorbance spectrum distinct from wild-type LITE-1: they both lost the 320 nm peak but retained normal absorption at 280 nm (FIG. 11A-B). Thus, the two mutations disrupted LITE-1's absorption of UVA but not UVB light. This is consistent with the fact that the genetic screen was targeted for isolating mutants defective in responding to UVA but not UVB light, since the optical system of the microscope used to evoke and assay phototaxis behavior did not transmit UVB light (Liu et al., 2010).

Figure 11H:
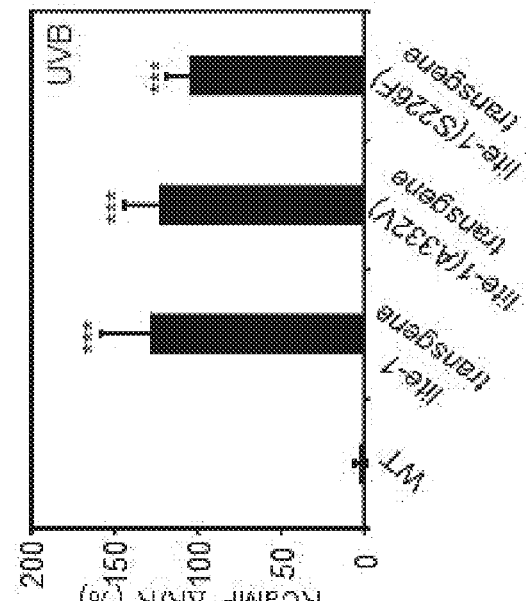
Figure 11G:
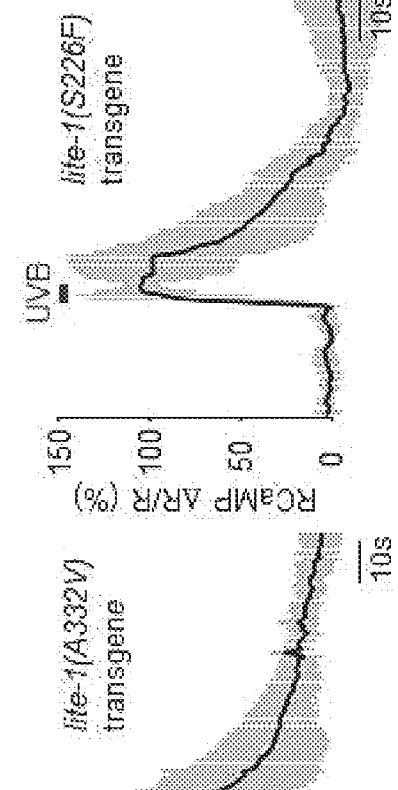
Figure 11F:
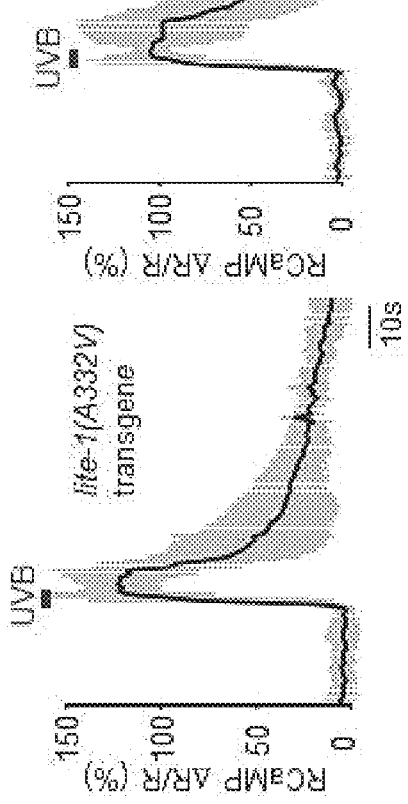

Given that LITE-1$^{A332V}$ and LITE-1$^{S226F}$ proteins retained normal absorption of UVB light in vitro, one would predict that these two mutant forms of LITE-1 shall preserve the sensitivity to UVB light in vivo. To test this idea, an optical path was set up through which UV light was directed to the worm directly. Indeed, though transgenic worms expressing these two mutant forms of LITE-1 were insensitive to UVA light (FIGS. 9A and 10A), they were nevertheless sensitive to UVB light (FIGS. 11C and 10B). In addition, as was the case with wild-type LITE-1, UVB light also induced robust calcium transients in muscle cells ectopically expressing these two mutant forms of LITE-1 (FIG. 11D-H). These results are in line with the data from spectral analysis (FIG. 11A-B). Thus, it appears that the absorption of UVA and UVB light by LITE-1 can be separated, and also provides further evidence demonstrating the specificity of LITE-1 photoabsorption.

Example VI

This example demonstrates that LITE-1 absorption of UVB but not UVA light shows resistance to photobleaching.

Figure 11I:
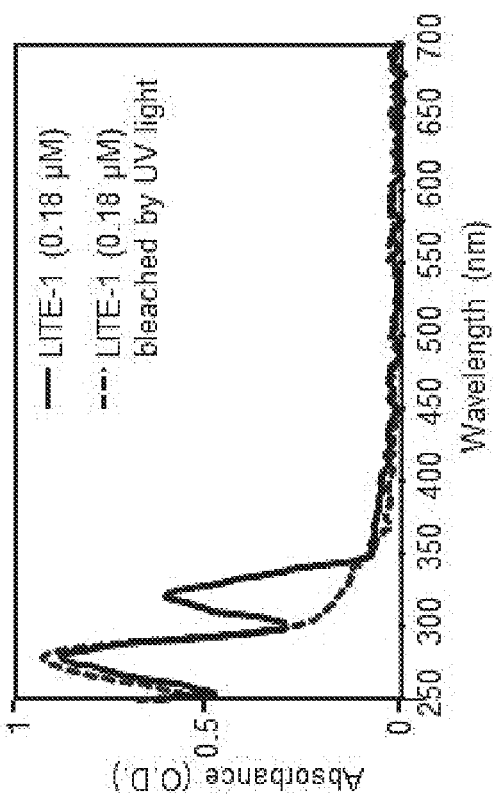

Prolonged light illumination bleaches photoreceptors (Wang and Montell, 2007, supra; Yau and Hardie, 2009, supra). Experiments tested this property of LITE-1, and it was found that pre-exposure to UV light can readily bleach LITE-1's ability to absorb UVA light by eliminating its 320 nm peak (FIG. 11I). Surprisingly, such treatment spared the 280 nm peak (FIG. 11I), indicating that the ability for LITE-1 to capture UVB light was more stable and relatively resistant to photobleaching. This experiment reveals an additional feature that distinguishes LITE-1 absorption of UVA and UVB light.

Example VII

This example demonstrates that two tryptophan residues are required for LITE-1 function.

The success in identifying residues critical for LITE-1's absorption of UVA light encouraged exploration of what may underlie its absorption of UVB light. Tryptophan residues show intrinsic absorption of UVB light, peaking at 280 nm. It is also known that light absorption by tryptophan is quite resistant to photobleaching (Wu et al., 2008, supra). These two features together led to experiments questioning whether tryptophan residues in LITE-1 play a role in mediating its absorption of UVB light. Six tryptophan residues are found in LITE-1 (FIG. 8I). However, should any of these tryptophan residues be important for LITE-1 function, they would not be expected to be picked up by the genetic screen, as the mutagen (EMS) used in the screen would typically mutate a tryptophan residue to a stop codon rather than generate a missense mutation.

Therefore, to test the above hypothesis, experiments were conducted that mutated each of the six tryptophan residues to alanine through site-directed mutagenesis and expressed the corresponding mutant forms of LITE-1 as a transgene in muscle cells. Experiments first examined their function in vivo. Two tryptophan residues, W77 and W328, when mutated to alanine, abolished the sensitivity of LITE-1 to UVA light in vivo in behavioral assays (FIGS. 12A and 13A), whereas mutating the other four tryptophan residues did not elicit a notable effect (FIG. 12A). Experiments obtained a similar result when mutating W77 and W328 to F (phenylalanine) (FIG. 12A). Furthermore, the two tryptophan mutations W77F and W328F nearly eliminated UVA light-induced calcium transients in muscle cells ectopically expressing LITE-1 (FIG. 12C-F). These data identify a critical role for W77 and W328 in LITE-1 function in vivo.

Lastly, experiments purified the two mutant forms of LITE-1, LITE-1$^{W77F}$ and LITE-1$^{W328F}$, to homogeneity (FIG. 9F-G), and examined their photoabsorption in vitro. Strikingly, W77F and W328F mutations not only abolished LITE-1's absorption of UVA light at 320 nm, but also nearly eliminated its absorption of UVB light at 280 nm (FIG. 12K-L). Consistently with this spectral data, it was found that these two tryptophan mutations abolished the sensitivity of LITE-1 to UVB light in vivo in behavioral assays (FIGS. 12B and 13B). In addition, UVB light elicited little, if any, calcium transients in muscle cells ectopically expressing these two mutant forms of LITE-1 (FIG. 12G-J). The residual responses arose from the other tryptophan residue. Thus, the two tryptophan residues W77 and W328 are critical for LITE-1 function both in vivo and in vitro. These experiments identify key molecular determinants required for LITE-1 function in vivo and in vitro.

Example VIII

This example demonstrates the genetic engineering of photoreceptors.

Figure 14:
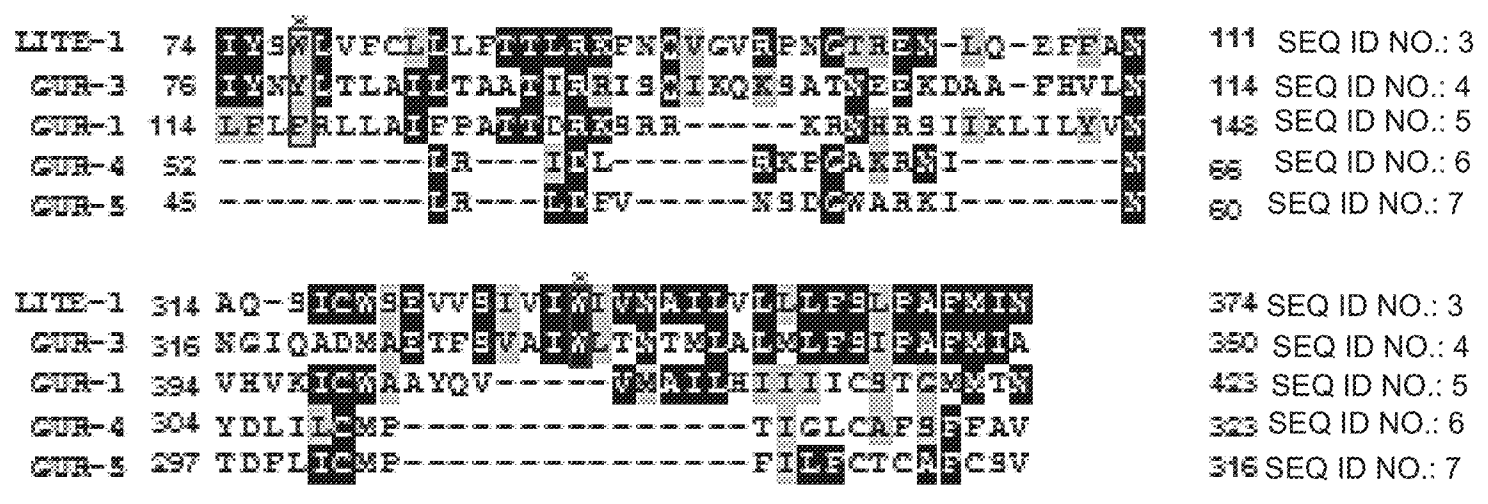

To provide further evidence supporting a critical role for the two tryptophan residues in mediating photoabsorption, it was wondered if introducing such tryptophan residues into another protein would promote photoabsorption. On the other hand, tryptophan residues alone cannot underpin the high photoabsorption capacity of LITE-1, and other parts of LITE-1 must be involved, which may serve as a "backbone" to support the function of the two tryptophan residues in capturing photons. It was thus reasoned that those proteins related to LITE-1, such as other GR genes, may possess such a backbone structure and thereby would have a higher likelihood to be engineered as a photoreceptor. The *C. elegans* GR family contains five members. With the exception of LITE-1, no other GR genes have both tryptophan residues at the corresponding positions (FIG. 14A). It was noticed that although GUR-3 is not that similar to LITE-1 at the sequence level (40% sequence identity with LITE-1), it has one tryptophan residue in place, which corresponds to W328 in LITE-1 (FIG. 14A). GUR-3 was contemplated to function as a chemoreceptor (Bhatla and Horvitz, Neuron 85, 804-818 2015). As expected, ectopic expression of GUR-3 in muscle cells did not promote their sensitivity to UV light in behavioral assays (FIGS. 8A, 14B, and 14F-G), indicating that GUR-3 is not photosensitive. Indeed, calcium imaging revealed that UV light evoked little, if any, calcium response in muscle cells ectopically expressing GUR-3 (FIGS. 8B-D and 14C-E). Experiments then mutated residue Y79 in GUR-3 to W (GUR-3$^{Y79W}$), which corresponds to W77 in LITE-1 (FIG. 14A). Strikingly, worms ectopically expressing the tryptophan-bearing GUR-3$^{Y79W}$ then became sensitive to UVB light (FIGS. 8A and 14G). UVA light was not effective on these worms (FIG. 14B-F). This result was expected, as UVA absorption by LITE-1 requires additional key elements such as residues A226 and S332 and perhaps others (FIG. 9A-E). Experiments also examined UVB light-evoked calcium transients in muscle cells, and found that ectopic expression of the tryptophan-bearing GUR-3$^{Y79W}$ greatly potentiated UVB light-induced calcium response in these cells (FIG. 8B-D). Thus, introducing a tryptophan residue into GUR-3 promotes photosensitivity.

Figure 8G:
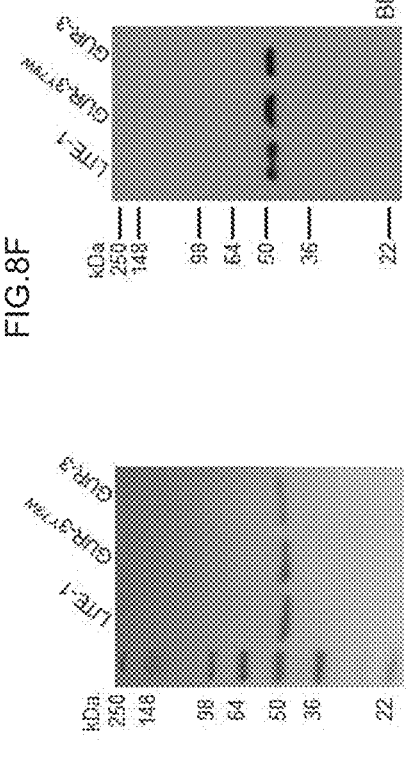
Figure 8H:
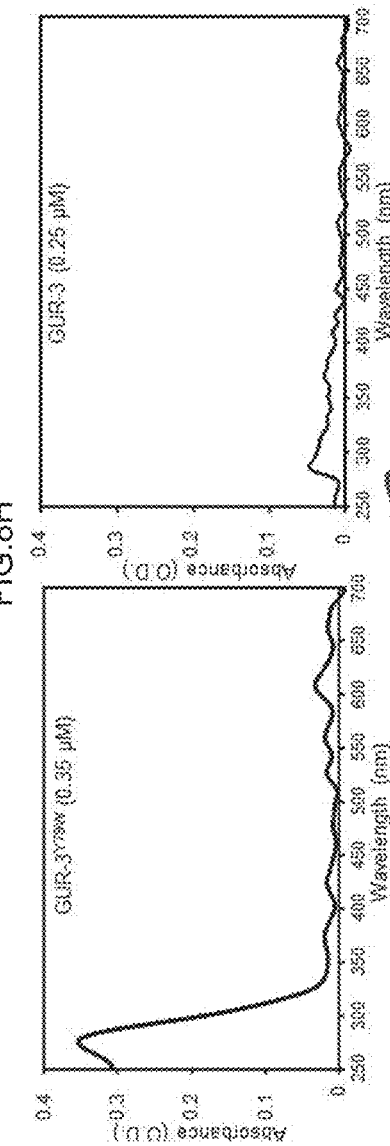
Figure 8I:
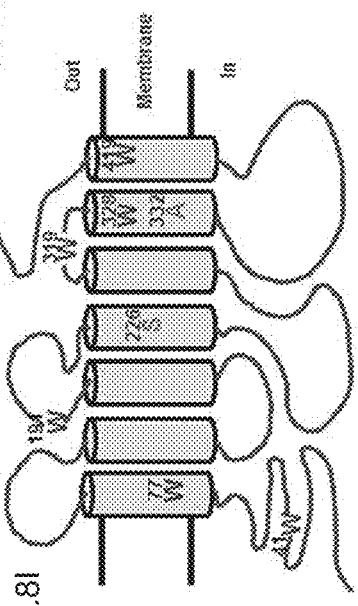

Having characterized the photosensitivity of GUR-3$^{Y79W}$ and GUR-3 in vivo, experiments then purified both proteins to homogeneity (FIG. 8E-F), and examined their photoabsorption in vitro (FIG. 8G-H). As expected, GUR-3 showed little, if any, absorption of UVB light (FIG. 8H). By contrast, strong absorption of UVB light at 280 nm was observed in GUR-3$^{Y79W}$ (FIG. 8G). The extinction coefficient of this tryptophan-bearing GUR-3$^{Y79W}$ protein reached the level of $10^6$ M$^{-1}$cm$^{-1}$ ($1.1 \times 10^6$ M$^{-1}$cm$^{-1}$), which is about one-third of that found for LITE-1. This data provides a biochemical basis for the observed photosensitivity of GUR-3$^{Y79W}$.

Example IX

This example describes the materials and methods for Examples I-VIII.

Experimental Model and Subject Details

*C. elegans* strains were maintained at 20° C. on nematode growth medium (NGM) plates seeded with OP50 bacteria. Liquid culture was used to produce large quantities of worms for protein purification. Transgenic lines were generated by injecting plasmid DNA directly into hermaphrodite gonad. Integrated transgenic strains were outcrossed at least six times before used for protein purification.

Immunofluorescence

Immunostaining was performed on primary cultured cells using standard protocols (Christensen et al., Neuron 33, 503-514 2002). Muscle cells co-express LITE-1 and GFP or express GFP alone as a transgene driven by the muscle-specific promoter myo-3. Gravid hermaphrodites were lysed to release eggs, and embryos were dissociated by chitinase treatment and trituration, filtered through a 5 µm membrane, plated on cover glasses coated with peanut lectin, and cultured in L15 with 10% serum (340-345 mOsm) at 20° C. To perform non-permeablized surface staining, live cells were first blocked with 3% BSA and 5% normal goat serum (NGS) in PBS for 30 min, and then incubated with primary antibodies (1 µg/ml) for one hour in PBS (1.5% BSA) at room temperature. Following three washes with PBS, cells were fixed for 10 min with 1.5% paraformaldehyde (PFA) in PBS followed by three washes with PBS and one hour incubation in second antibodies (1:2000, Cy3 conjugated). After five washes with PBS, cover glasses were mounted for imaging analysis. To perform permeabilized staining, cells were first fixed with 1.5% PFA in PBS for 10 min at room temperature, rinsed three times with PBS, and permeabilized with 0.5% Trition X-100 in PBS for 5 min. After three washes with PBS, cells were blocked with BSA and NGS, incubated with primary antibodies, and washed five times. Following one hour incubation with secondary antibodies, cover glasses were rinsed five times before mounting. The N- and C-terminal end peptides (15 residues) were used to immunize rabbits to generate LITE-1 antibodies which were affinity-purified before use for staining (YenZym Antibodies).

Protein Purification and Spectrophotometric Analysis

Worms were cultured in the dark. They were first cultured on NGM plates and then transferred to 10 litter of S medium for liquid culture using a fermenter (New Brunswick, 20° C., 50% dissolved oxygen, 300 rpm agitation, pH7.2) with the support from concentrated HB101 bacteria. After 2 generations (about 7-8 days) in the fermenter, worms were harvested and suspended in 80 ml of 25 mM bis-trsi-propane BTP buffer (pH7.2) supplemented with proteinase inhibitor cocktail (Complete Mini, EDTA-free). All purification steps were carried out in the dark. A microfluidizer (Microfluidics Inc.) was used to break the worms (120 psi, 5 cycles). After removing the debris by low speed centrifugation at 1,000 g for 10 min at 4° C., the supernatant was collected and centrifuged again at high speed (100,000 g) for 1 h at 4° C. to pellet cell membranes, which were solubilized with 20 mM n-dodecyl-β-D-maltopyranoside (DDM; Affymentrix) in BTP buffer (pH7.2) containing 500 mM NaCl. After removing unsolubilized materials by centrifugation at 40,000 g for 30 min, the extract was loaded to an a1D4 affinity column. Note: an 1D4 tag was attached to the C-terminus of LITE-1 and GUR-3 expressed as a transgene in the worm muscle, as described for $A_{2A}$ receptor (Salom et al., 2012, supra). Bovine rhodopsin (Rho) has this tag sequence at its C-terminus. After washing with the washing buffer (10 mM DDM in 25 mM BTP buffer [pH7.2] and 500 mM NaCl), LITE-1 was eluted with 1.5 mg/ml of 1D4 peptide diluted in this buffer. Purified LITE-1 was loaded onto a molecular size separation column (GE healthcare Bio-Sciences) to remove 1D4 peptide before spectrophotometric analysis. When purifying bovine rhodopsin (Rho), 2 mM 9-cis-retinal was used to resuspend pelleted cell membranes and incubate for 30 min prior to solubilization with DDM. This treatment was not performed when purifying LITE-1, GUR-3, or $A_{2A}$ receptor. Purified protein samples used for SDS-PAGE were prepared under non-reducing conditions at room temperature (no heating) to avoid aggregation.

The concentration of purified proteins was first determined by the Bradford assay (Bio-Rad Inc.), and then verified by SDS-PAGE followed by coomassie staining using rhodopsin as a standard. The concentration data were also independently verified by silver staining following SDS-PAGE using rhodopsin as a standard.

Spectrophotometric analysis was performed on a UV-Vis spectrophotometer (Varian Cary 50) in a quartz cuvette. Samples and reference blanks were all diluted in the same washing buffer. Note: 1D4 peptide was removed from samples prior to spectrophotometric analysis (see above). For those experiments involving treatment with denaturing agents or $H_2O_2$, LITE-1 was incubated with these agents for 5 min at room temperature prior to spectrophotometric analysis. All the assays were carried out in the dark.

Behavior, calcium imaging and molecular biology

Body paralysis assay was performed on day 1 gravid adult hermaphrodites, which were raised on NGM plates, under a Zeiss fluorescence dissection scope (Zeiss Discovery) coupled with an M2Bio lens system from Kramer Scientifics. The assay was done on NGM plates without OP50 using a protocol similar to that for assaying phototaxis behavior (Liu et al., 2010, supra; Ward et al., 2008, supra). UVA light pulses (350±20 nm, 0.8 mW/mm2, up to 20 sec) were delivered from an Arc lamp (X-Cite 120) to the worm through a 10×lens in combination with 2.5×zoom. To deliver UVB light, a 280±10 nm excitation filter (from Semrock, 0.03 mW/mm2) was attached to the end of the liquid light guide of the lamp, which was then directly pointed to the worm using a micromanipulator. The dish was manually moved to keep the worm in the view field. In another assay, body paralysis was quantified by monitoring locomotion speed decrease over time using the Wormlab system (MBF Biosciences). UVA and UVB light was directed to the worm using a liquid light guide as described above. To minimize the effect of endogenous lite-1 gene on locomotion speed under UV light (Liu et al., 2010, supra), this assay was performed in lite-1(xu7) mutant background for all genotypes. A total of 20-50 animals were assayed for each genotype in each experiment unless otherwise indicated. The sample size of each assay was found to be adequate after running power analysis (P>0.8). Each worm was assayed five times, and once the worm was paralyzed, the assay was stopped to let it recover for next round of test.

Calcium imaging of muscle cells was performed on an inverted microscope (Olympus IX73) under a 60×lens as previously described (Li et al., Cell 159, 751-765 2014; Xiao et al., Cell 152, 806-817 2013). RCaMP was expressed as a transgene in muscle cells using the myo-3 promoter. YFP was also expressed as a transgene under the same promoter to enable ratiometric imaging. Worms were glued on an agarose pad and bathed in solution (10 mM HEPES [pH 7.4], 5 mM KCl, 145 mM NaCl, 1.2 mM $MgCl_2$, 2.5 mM CaCl$_2$, and 10 mM glucose). UV light (UVA: 340±20 nm, 0.7 mW/mm2; UVB: 280±10 nm, 0.02 mW/mm2; 5 sec) was directly projected to the worm through a liquid light guide mounted on a micromanipulator. Images were acquired with a Roper Cool Snap CCD camera and processed with MetaFluor software (Molecular Devices). To minimize the contribution from endogenous photosensation system, all genotypes, including WT, carried lite-1(xu7) mutation in the background (Liu et al., 2010). The peak percentage change in the ratio of RCaMP/YFP fluorescence was quantified.

All the LITE-1 and GUR-3 constructs carry a 1D4 tag at the C-terminus, with the exception in FIG. 1 where no such a tag was included to LITE-1. Myc tag was only included in the construct used in FIG. 1B. Many plasmids contain an SL2::YFP fragment, which directs expression of YFP as a co-expression marker in muscle cells. SL2 achieves a role analogous to that played by IRES in mammalian expression vectors.

Quantification and Statistical Analysis

Quantification and statistical parameters were indicated in the legends of each figure, including error bars (SEM), n numbers, and p values. For those involving multiple group comparisons, ANOVA was applied, followed by a post hoc test. p values of <0.05 were considered significant.

INCORPORATION BY REFERENCE

The entire disclosure of each of the patent documents and scientific articles referred to herein is incorporated by reference for all purposes.

EQUIVALENTS

The disclosure may be embodied in other specific forms without departing from the spirit or essential characteristics thereof. The foregoing embodiments are therefore to be considered in all respects illustrative rather than limiting the disclosure described herein. Scope of the disclosure is thus indicated by the appended claims rather than by the foregoing description, and all changes that come within the meaning and range of equivalency of the claims are intended to be embraced therein.

We claim:

1. A composition, comprising:
   a) a LITE-1 polypeptide covalently linked to an affinity tag; and b) at least one carrier.

2. The composition of claim 1, wherein said affinity tag is selected from the group consisting of Myc, FLAG, and 1D4.

3. The composition of claim 2, wherein said affinity tag is 1D4.

4. The composition of claim 1, wherein said LITE-1 is wild type *C. elegans* LITE-1.

5. The composition of claim 1, wherein said LITE-1 is selected from the group consisting of SEQ ID NO:1 and sequences at least 90% identical to SEQ ID NO:1.

6. The composition of claim 1, wherein said LITE-1 is selected from the group consisting of SEQ ID NO:1 and sequences at least 95% identical to SEQ ID NO:1.

7. The composition of claim 1, wherein said LITE-1 is selected from the group consisting of SEQ ID NO:1 and sequences at least 99% identical to SEQ ID NO:1.

8. The composition of claim 1, wherein said carrier is a pharmaceutically acceptable carrier.

9. The composition of claim 1, wherein said carrier comprises one or more carriers selected from the group consisting of preservatives, emollients, emulsifying agents, surfactants, moisturizers, gelling agents, thickening agents, conditioning agents, film-forming agents, stabilizing agents, anti-oxidants, texturizing agents, gloss agents, mattifying agents, solubilizers, pigments, dyes, and fragrances.

10. The composition of claim 1, wherein said composition is selected from the group consisting of a pharmaceutical composition, a cosmetic composition, a sunscreen, a moisturizer, a gel, an ointment, a stick, a cream, and a lotion.

11. The composition of claim 1, wherein said composition is formulated for topical administration.

12. The composition of claim 1, wherein said composition is formulated for industrial utilization.

13. The composition of claim 12, wherein said composition is selected from the group consisting of a film and a coating.

14. The composition of claim 12, wherein said carrier is a polymer or plastic.

15. A composition comprising a nucleic acid encoding a LITE-1 polypeptide linked to an affinity tag.

16. A method of purifying a LITE-1 polypeptide, comprising:
   a) contacting a composition comprising a LITE-1 polypeptide covalently linked to an affinity tag with an antibody that specifically binds to said affinity tag;
   b) isolating said antibody bound to said affinity tag; and
   c) cleaving said LITE-1 polypeptide from said affinity tag, thereby purifying said LITE-1 polypeptide.

17. The method of claim 16, wherein said antibody is a monoclonal antibody.

18. The method of claim 16, wherein said affinity tag is selected from the group consisting of Myc, FLAG, and 1D4.

19. The method of claim 16, wherein said LITE-1 polypeptide is wild type LITE-1.

* * * * *